United States Patent [19]

Boden et al.

[11] 4,395,370

[45] Jul. 26, 1983

[54] BRANCHED CHAIN ALKENYL METHYL CARBONATES, USES THEREOF IN AUGMENTING OR ENHANCING THE AROMA OF PERFUME COMPOSITIONS, COLOGNES AND PERFUMED ARTICLES AND FORMATE INTERMEDIATES USEFUL IN PREPARING SAME

[75] Inventors: Richard M. Boden, Monmouth Beach; Theodore J. Tyszkiewicz, Sayreville; Michael Licciardello, Farmingdale, all of N.J.

[73] Assignee: International Flavors & Fragrances Inc., New York, N.Y.

[21] Appl. No.: 329,222

[22] Filed: Dec. 10, 1981

[51] Int. Cl.$^3$ .................... C07C 69/96; A61K 7/46
[52] U.S. Cl. .................. 260/463; 252/8.8; 252/132; 252/194.11; 252/522 R; 424/69; 424/70; 424/71; 560/261
[58] Field of Search .................. 260/463; 560/261

[56] References Cited

U.S. PATENT DOCUMENTS

| | | | |
|---|---|---|---|
| 2,806,874 | 9/1957 | Surmantis | 560/261 |
| 4,033,993 | 7/1977 | Bruns et al. | 260/463 |
| 4,080,309 | 3/1978 | Bruns et al. | 260/463 |
| 4,338,170 | 7/1982 | Murata et al. | 560/261 |

OTHER PUBLICATIONS

Chemical Abstracts, Seventh Collective Index, 1962–66, Subjects Bf–Cho, "Carbonic Acid".

*Primary Examiner*—Donald G. Daus
*Assistant Examiner*—M. C. Eakin
*Attorney, Agent, or Firm*—Arthur L. Liberman

[57] ABSTRACT

Described are branched chain alkenyl methyl carbonates and branched chain alkenyl formates defined according to the structure:

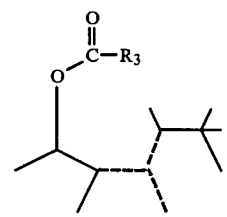

wherein $R_3$ represents hydrogen or methoxy and wherein in each of the molecules described by the structure, one of the dashed lines is a carbon-carbon double bond and each of the other of the dashed lines is a carbon-carbon single bond; and uses of the compounds wherein $R_3$ is methoxy in augmenting or enhancing the aroma of perfume compositions, colognes and perfumed articles such as solid or liquid anionic, cationic, nonionic or zwitterionic detergents, fabric softener compositions, fabric softener articles, hair sprays, shampoos, bath oils and plastic fragrances.

2 Claims, 30 Drawing Figures

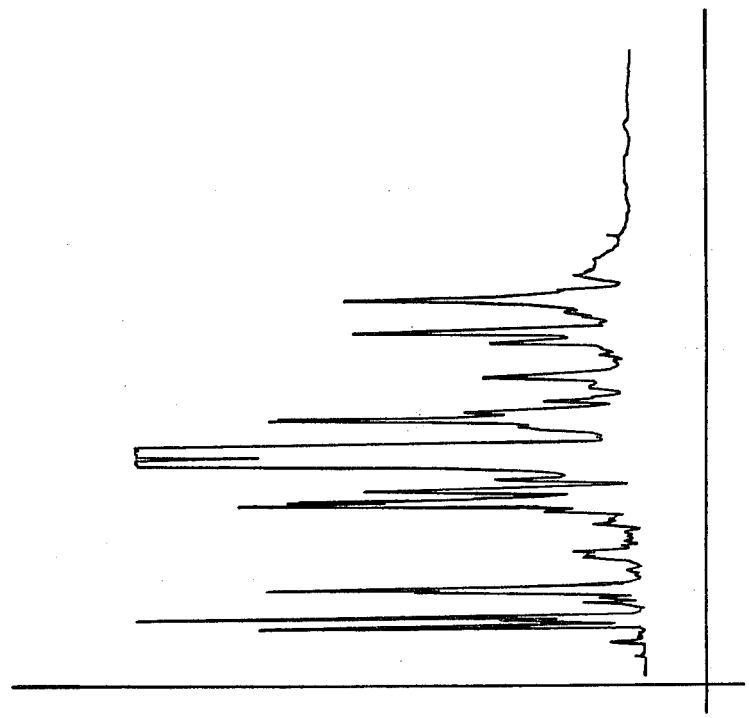
FIG.AC
GLC PROFILE FOR EXAMPLE A.
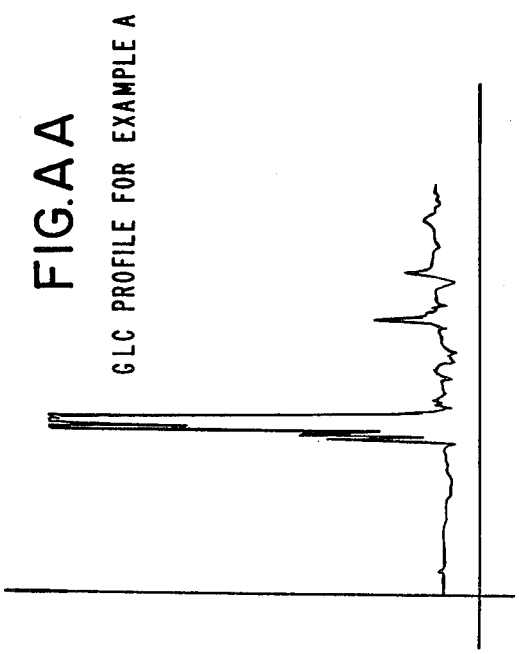
FIG.AA
GLC PROFILE FOR EXAMPLE A
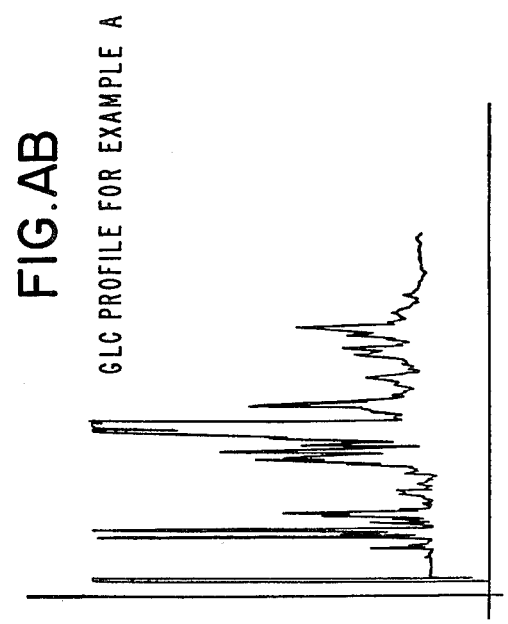
FIG.AB
GLC PROFILE FOR EXAMPLE A

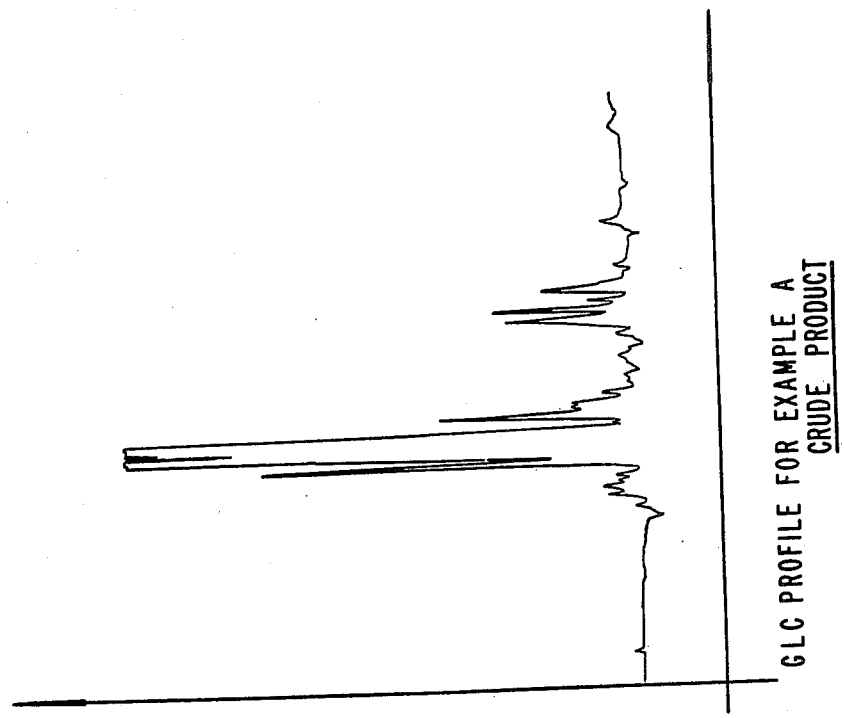
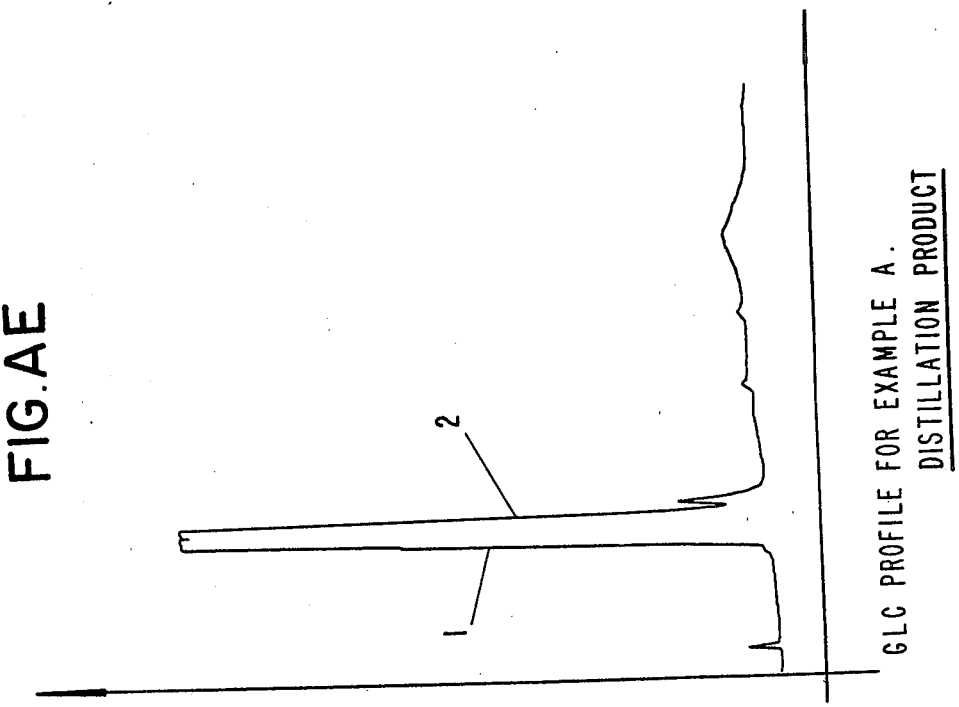

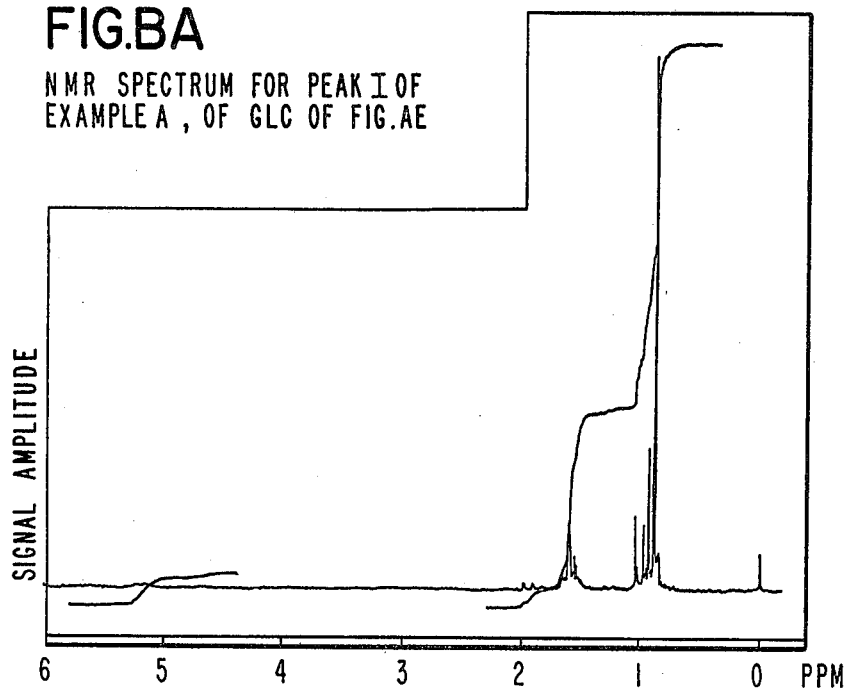
FIG.BA
NMR SPECTRUM FOR PEAK I OF EXAMPLE A, OF GLC OF FIG.AE
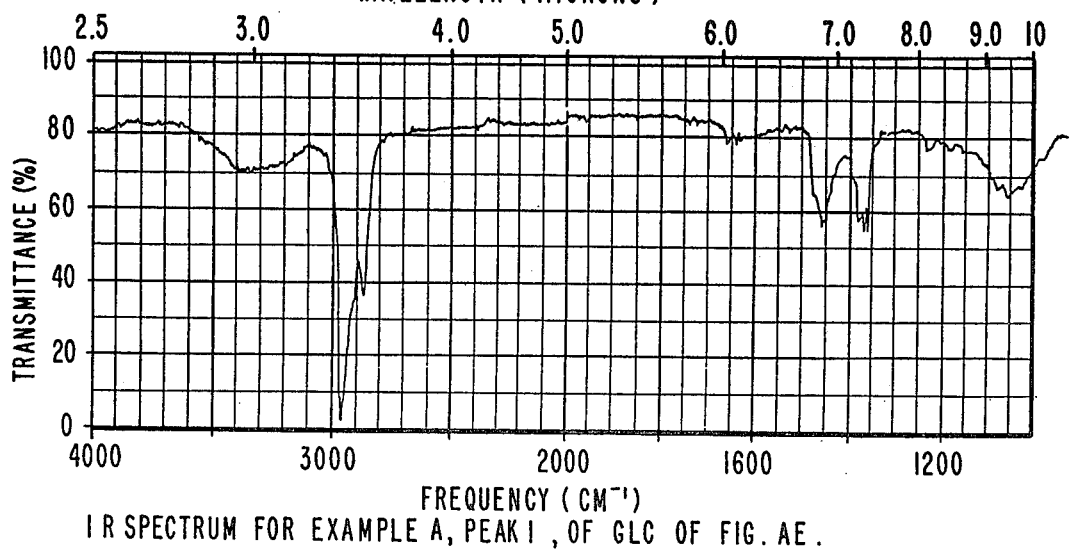
IR SPECTRUM FOR EXAMPLE A, PEAK I, OF GLC OF FIG.AE.
FIG.BB

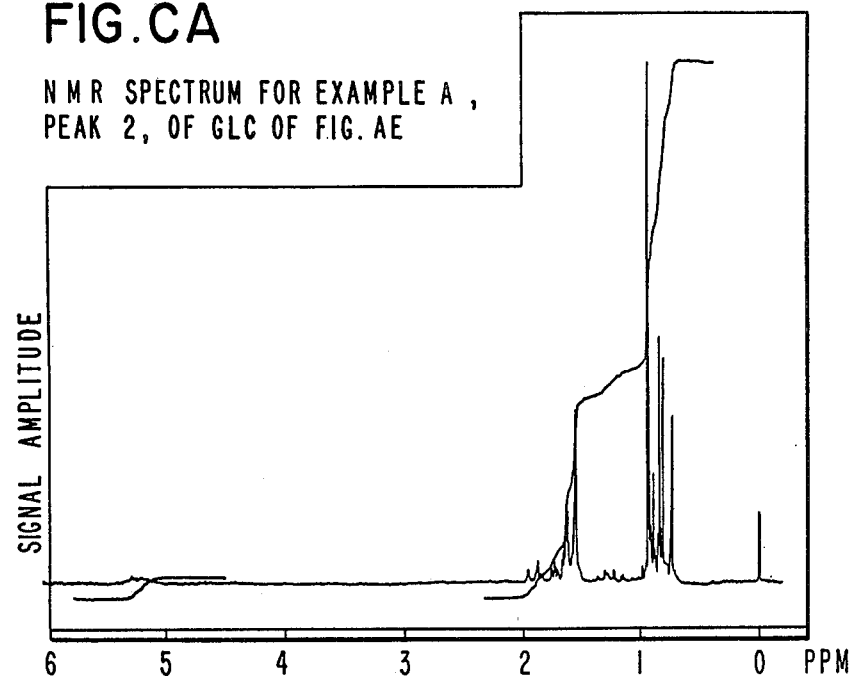
FIG.CA
NMR SPECTRUM FOR EXAMPLE A, PEAK 2, OF GLC OF FIG. AE
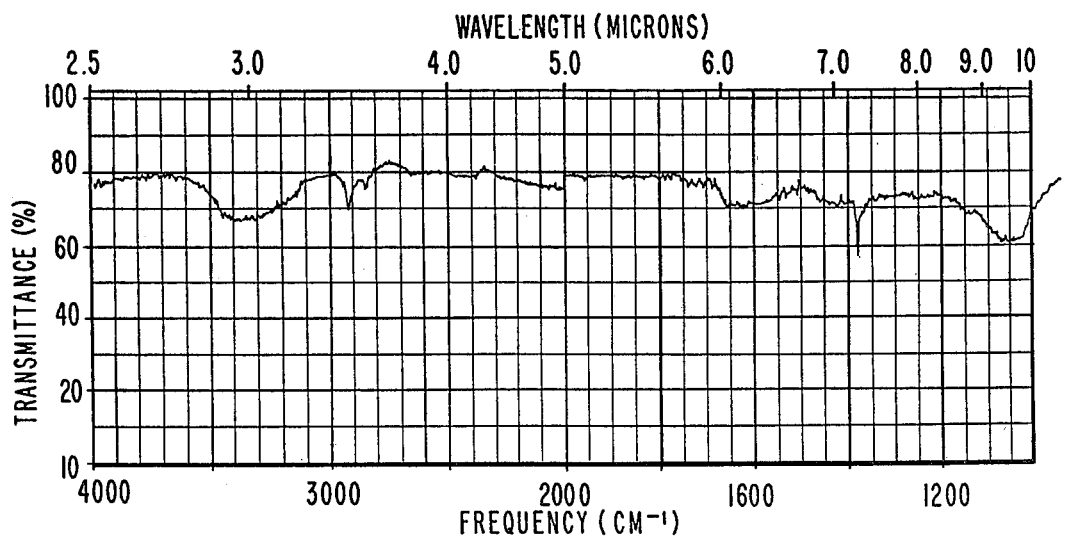
IR SPECTRUM FOR EXAMPLE I, PEAK 2 OF GLC OF FIG.AE
FIG.CB

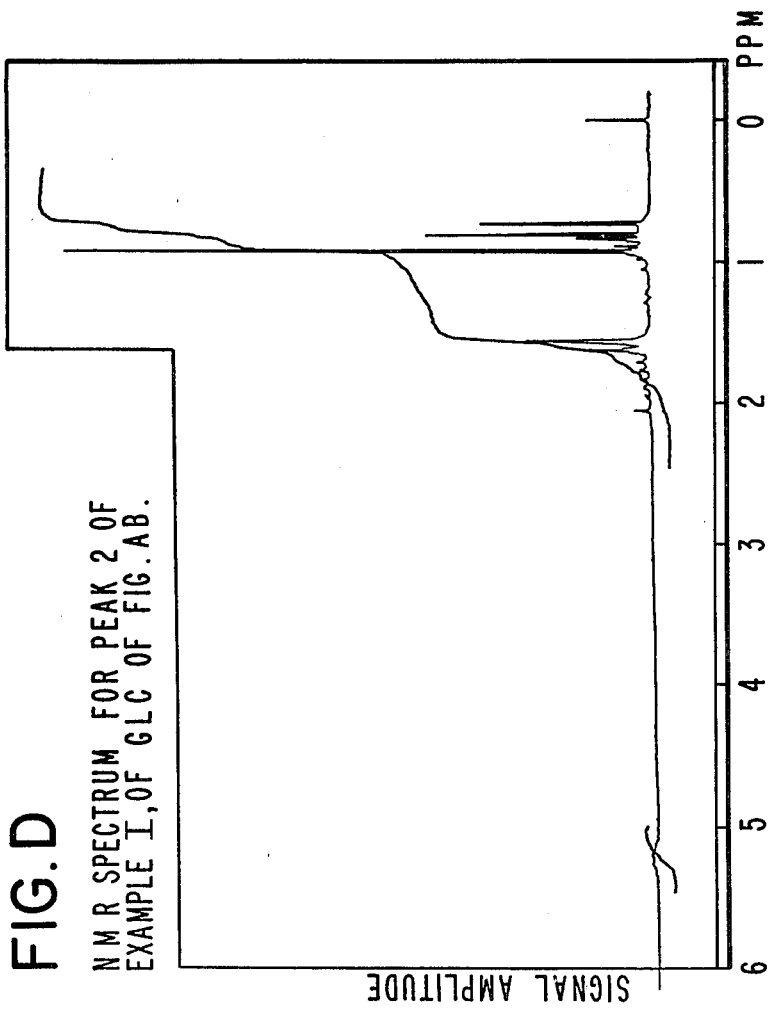
FIG. D
NMR SPECTRUM FOR PEAK 2 OF EXAMPLE I, OF GLC OF FIG. AB.

GLC PROFILE FOR EXAMPLE I

IR SPECTRUM FOR PEAK 3 OF EXAMPLE I

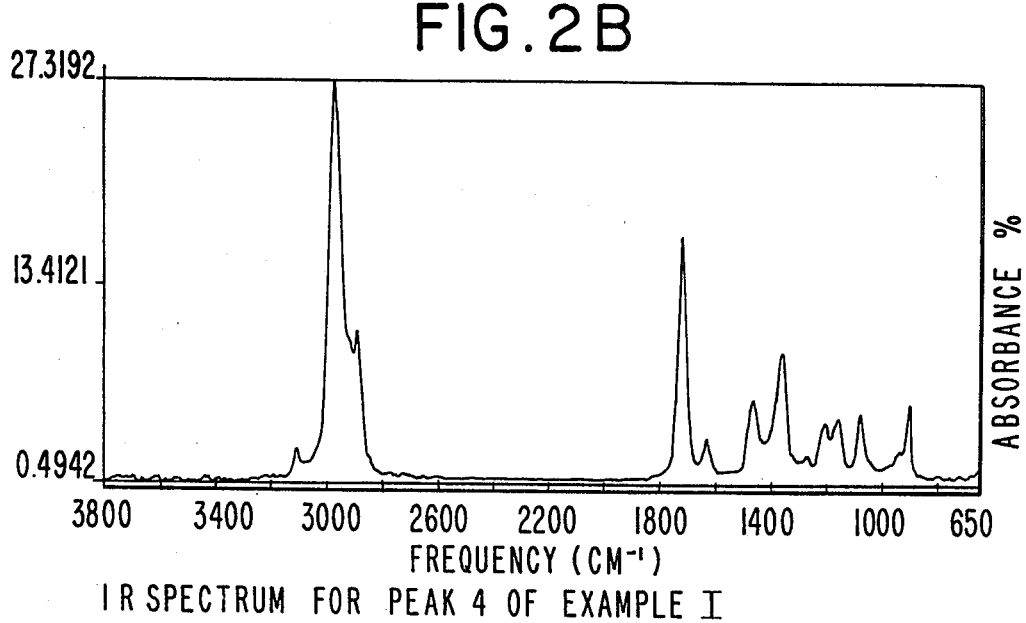
IR SPECTRUM FOR PEAK 4 OF EXAMPLE I
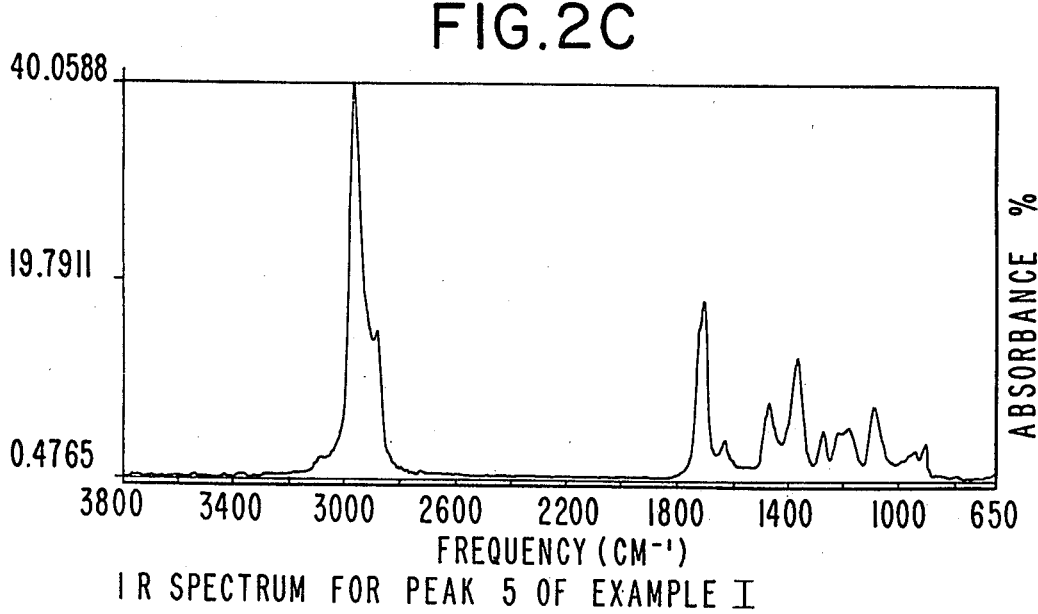
IR SPECTRUM FOR PEAK 5 OF EXAMPLE I

IR SPECTRUM FOR PEAK 6 OF EXAMPLE I.

IR SPECTRUM FOR PEAK 7 OF EXAMPLE I

IR SPECTRUM FOR PEAK 8 OF EXAMPLE I.

IR SPECTRUM FOR PEAK 9 OF EXAMPLE I.

IR SPECTRUM FOR PEAK 10 OF EXAMPLE I.

NMR SPECTRUM FOR EXAMPLE I

NMR SPECTRUM FOR EXAMPLE I

NMR SPECTRUM FOR EXAMPLE I

GLC PROFILE FOR EXAMPLE II(A).

GLC PROFILE FOR EXAMPLE II(B).

GLC PROFILE FOR EXAMPLE III.

FIG. 7
GLC PROFILE FOR EXAMPLE IV(A).
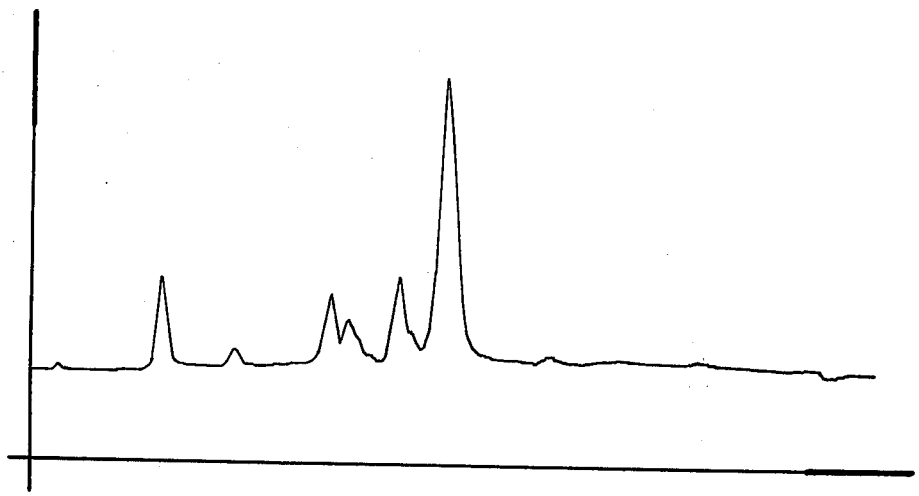
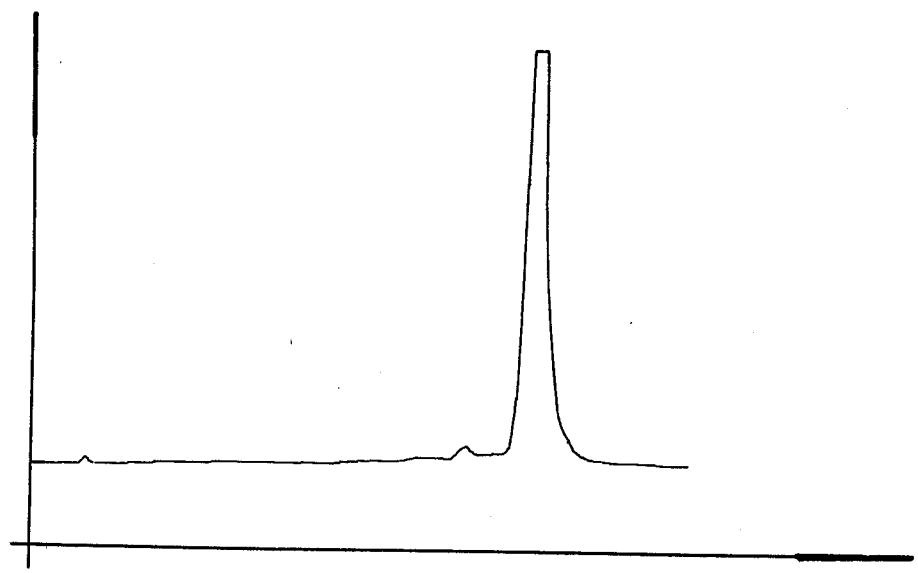
GLC PROFILE FOR FRACTION 5 OF
EXAMPLE IV(B).
FIG. 8

IR SPECTRUM FOR FRACTION 5 OF EXAMPLE IV (B).

BRANCHED CHAIN ALKENYL METHYL CARBONATES, USES THEREOF IN AUGMENTING OR ENHANCING THE AROMA OF PERFUME COMPOSITIONS, COLOGNES AND PERFUMED ARTICLES AND FORMATE INTERMEDIATES USEFUL IN PREPARING SAME

BACKGROUND OF THE INVENTION

The instant invention provides novel, branched chain alkenyl carbonates and formate intermediate for producing same defined according to the generic structure:

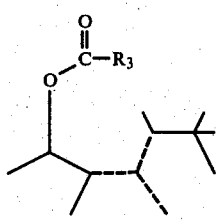

wherein $R_3$ represents hydrogen or methoxy and wherein in each of the molecules defined by the structure, one of the dashed lines represents a carbon-carbon double bond and each of the other of the dashed lines represent carbon-carbon single bonds, and in the compounds wherein $R_3$ is methoxy, uses thereof in augmenting or enhancing the aroma of consumable materials.

Materials which can provide myrrh-like and labdanum-like aroma nuances are well known in the art of perfumery. Many of the natural substances which provide such fragrances and contribute the desired nuances to perfumery compositions are high in cost, vary in quality from one batch to another and/or are generally subject to the usual variations of natural products.

The prior art contains a large number of teachings regarding the use of organic carbonates in augmenting or enhancing the aroma of perfumes. Thus, U.S. Pat. No. 4,033,993 discloses the use of organic carbonates defined according to the structure:

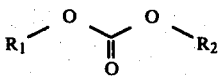

wherein $R_1$ is a moiety having from 8 to 12 carbon atoms selected from the group consisting of alkylcyclohexyl, alkenylcyclohexyl, alkynylcyclohexyl and cycloalkyl and $R_2$ is a moiety selected from the group consisting of alkyl having from 1 to 5 carbon atoms, alkenyl having from 2 to 5 carbon atoms and alkynyl having from 2 to 5 carbon atoms. U.S. Pat. No. 4,033,993 describes, for example, methyl-1-ethynycyclohexyl carbonate having a fruity, herbal complex odor and distinct fragrance of dill. In addition, U.S. Pat. No. 4,033,993 describes methyl cyclooctyl carbonate as having an herbal, natural and complex fragrance which is distinguished by a strong and long clinging flowery jasmine scent and further indicates its use in jasmine perfume compositions. U.S. Pat No. 4,033,993 describes the preparation of the compounds defined according to the structure:

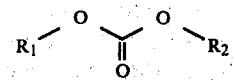

according to the reaction:

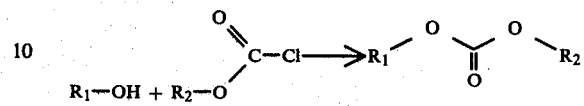

where $R_1$ and $R_2$ are defined as above.

In addition, U.S. Pat. No. 4,080,309 describes the perfume use of the carbonates defined according to the structure:

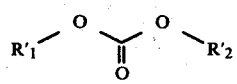

wherein $R_1'$ is a moiety having from 8 to 12 carbon atoms selected from the group consisting of alkylcyclohexyl, alkenylcyclohexyl, alkynylcyclohexyl and cycloalkyl and $R_2'$ is a moiety selected from the group consisting of alkyl having from 1 to 5 carbon atoms, alkenyl having from 2 to 5 carbon atoms and alkynyl having from 2 to 5 carbon atoms. Described in U.S. Pat. No. 4,080,309 are also such compounds as methyl cyclooctyl carbonate and the use thereof in jasmine perfume formulations. As is the case in U.S. Pat. No. 4,033,993, the carbonates of U.S. Pat. No. 4,080,309 are indicated to be prepared according to the reaction:

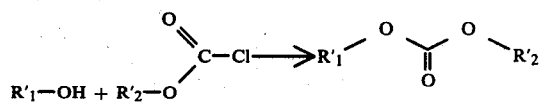

Nothing in the prior art, however, discloses the branched chain alkenyl methyl carbonates having the specific fragrance nuances of our invention and nothing in the prior art discloses the branched chain alkenyl formates which are useful as intermediates for preparing such carbonates.

BRIEF DESCRIPTION OF THE DRAWINGS

FIG. AA represents the GLC profile for the reaction product of Example A using a 70% sulfuric acid catalyst at 35° C.

FIG. AB represents the GLC profile for the reaction product of Example A using an Amberlyst ® 15 acidic ion exchange resin catalyst at a temperature of 150° C.

FIG. AC represents the GLC profile for the reaction product of Example A using an Amberlyst ® 15 catalyst at 100° C.

FIG. AD represents the GLC profile for the reaction product of Example A using a sulfuric acid catalyst and an alpha-methyl styrene diluent at 35° C. according to the conditions of United Kingdom Patent Specification No. 796,130 (crude reaction product).

FIG. AE represents the GLC profile for the reaction product of Example A using a sulfuric acid catalyst at 35° C. and an alpha-methyl styrene diluent according to the conditions of United Kingdom Patent Specification No. 796,130 (distilled reaction product). Distillation range: 36°–40° C. vapor temperature; 74°–94° C. liquid temperature and 4–5 mm/Hg pressure.

FIG. BA represents the NMR spectrum for peak 301 of the GLC profile of FIG. AE. Peak 301 has been determined by analysis to be the compound having the structure:

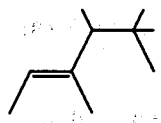

FIG. BB represents the infra-red spectrum for peak 301 of the GLC profile of FIG. AE.

FIG. CA represents the NMR spectrum for peak 302 of the GLC profile of FIG. AE. Peak 302 contains the compounds having the structures:

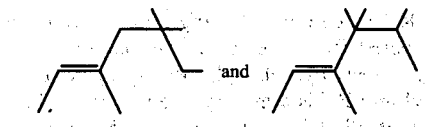

FIG. CB represents the infra-red spectrum for peak 302 of the GLC profile of FIG. AE.

FIG. D represents the NMR spectrum for peak 302 of the GLC profile of FIG. AB.

Figure 1:
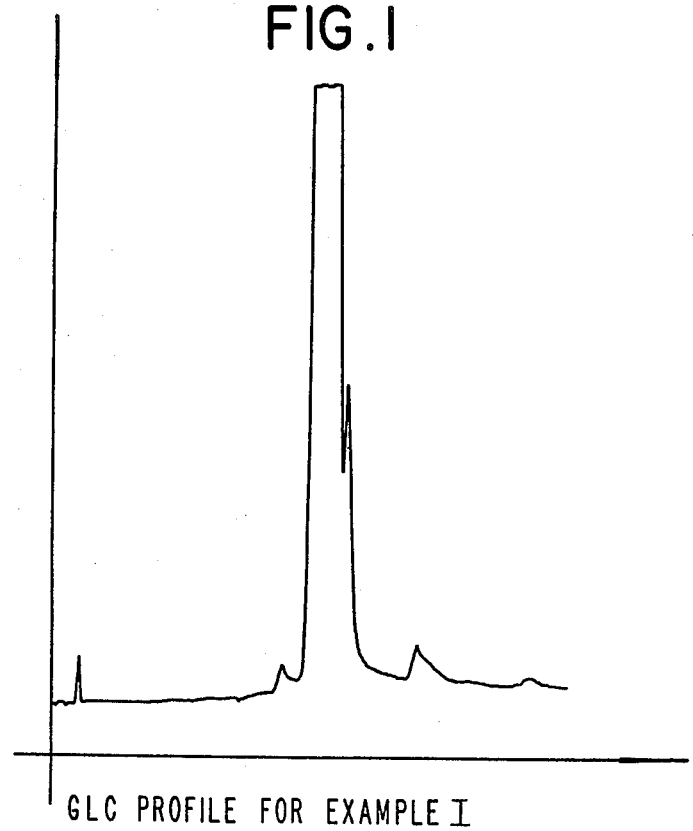

FIG. 1 set forth the GLC profile for the reaction product of Example I, containing compounds defined according to the structure: t,61

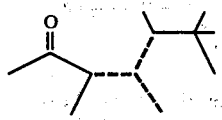

wherein in each molecule of the mixture, one of the dashed lines is a carbon-carbon double bond and the other of the dashed lines are carbon-carbon single bonds.

Figure 2A:
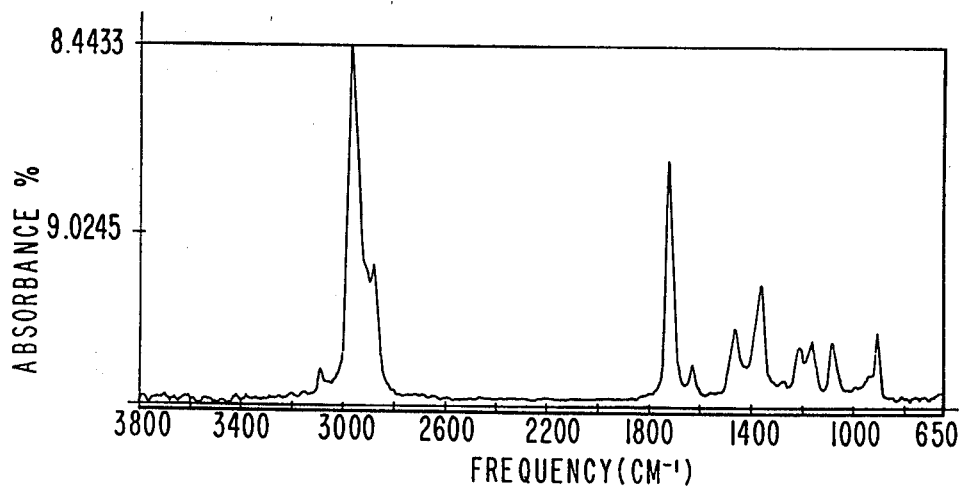

FIG. 2A represents the infra-red spectrum of Peak 3 of the GLC profile of FIG. 1.

FIG. 2B represents the infra-red spectrum of Peak 4 of the GLC profile of FIG. 1.

FIG. 2C represents the infra-red spectrum for Peak 5 of the GLC profile of FIG. 1.

Figure 2D:
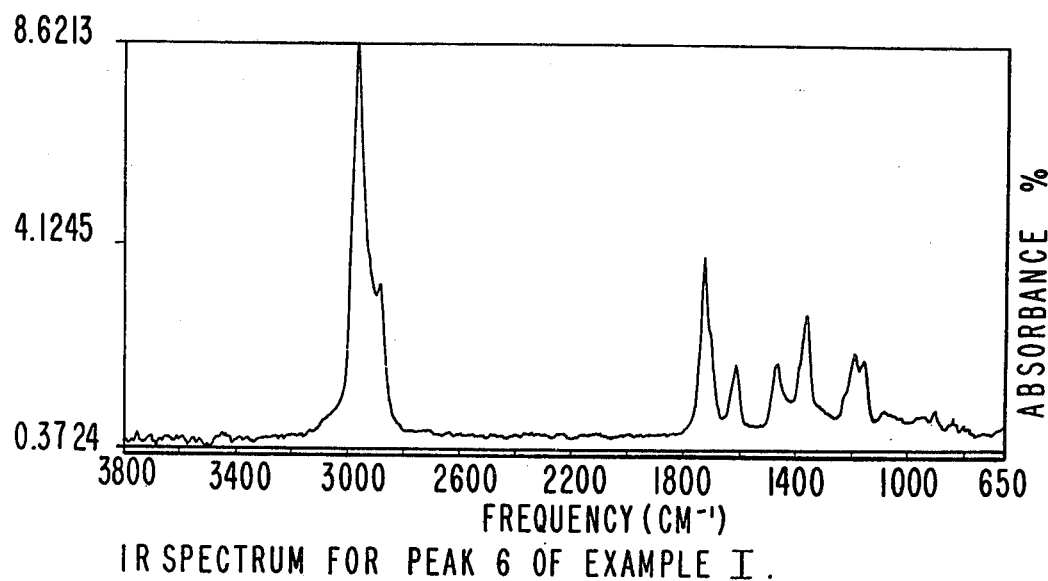

FIG. 2D represents the infra-red spectrum for Peak 6 of the GLC profile of FIG. 1.

Figure 2E:
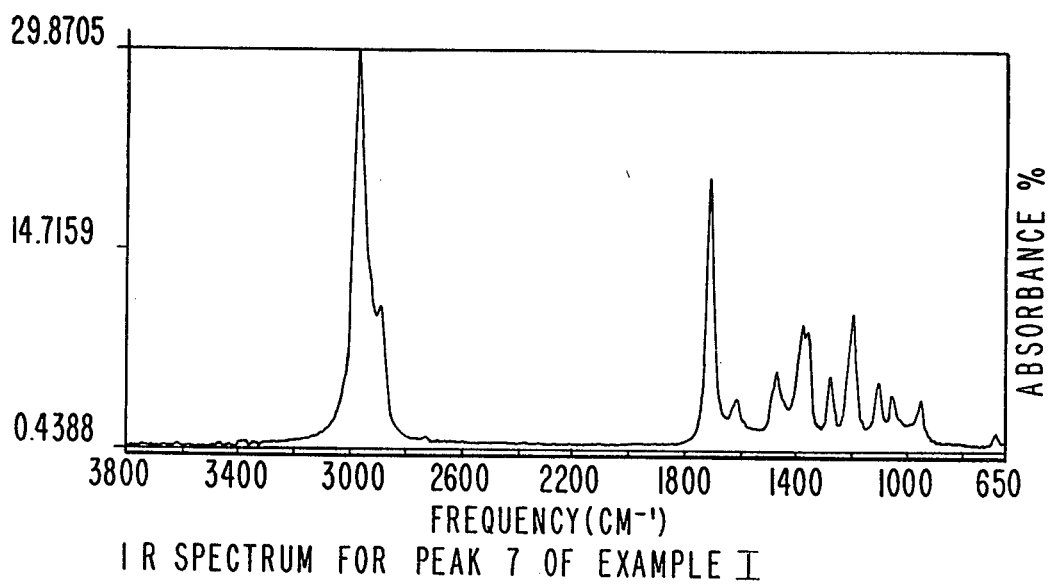

FIG. 2E represents the infra-red spectrum for Peak 7 of the GLC profile of FIG. 1.

Figure 2F:
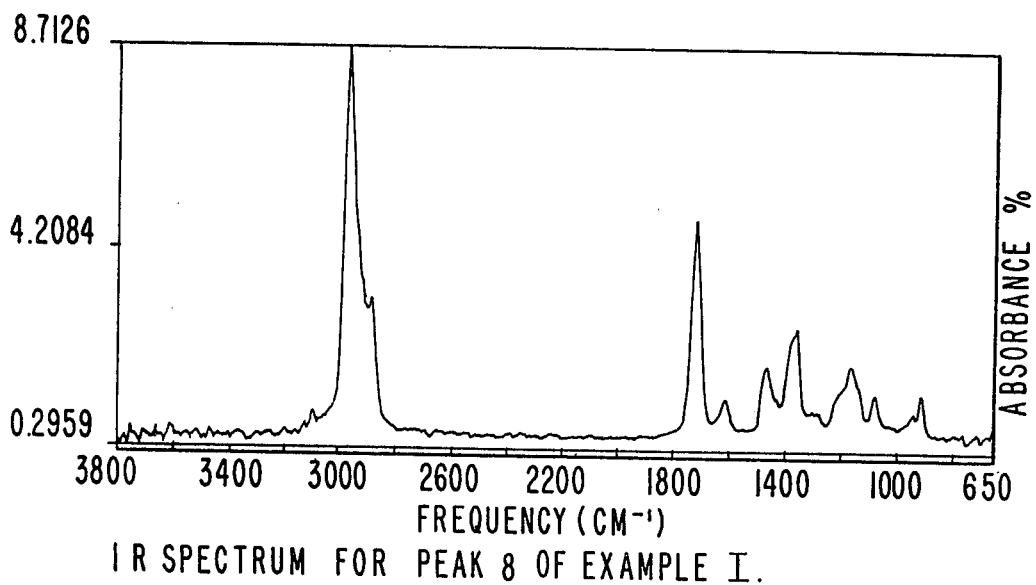

FIG. 2F represents the infra-red spectrum for Peak 8 of the GLC profile of FIG. 1.

Figure 2G:
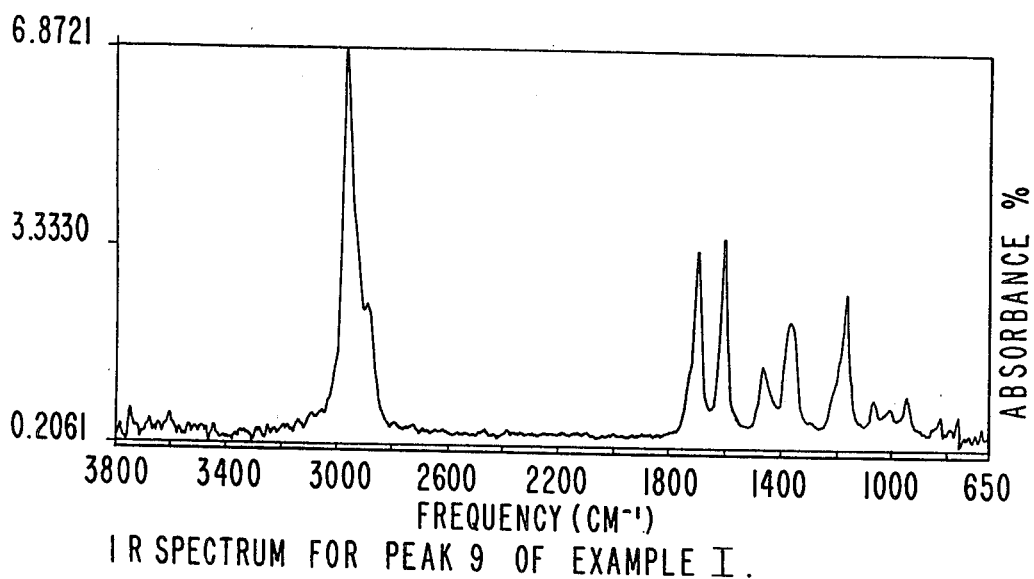

FIG. 2G represents the infra-red spectrum for Peak 9 of the GLC profile of FIG. 1.

Figure 2H:
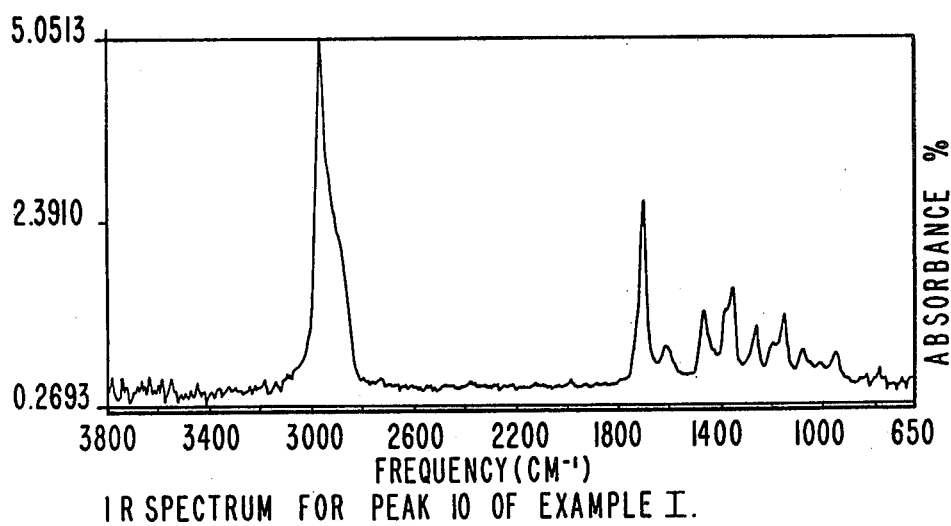

FIG. 2H represents the infra-red spectrum for Peak 10 of the GLC profile of FIG. 1.

Figure 2J:
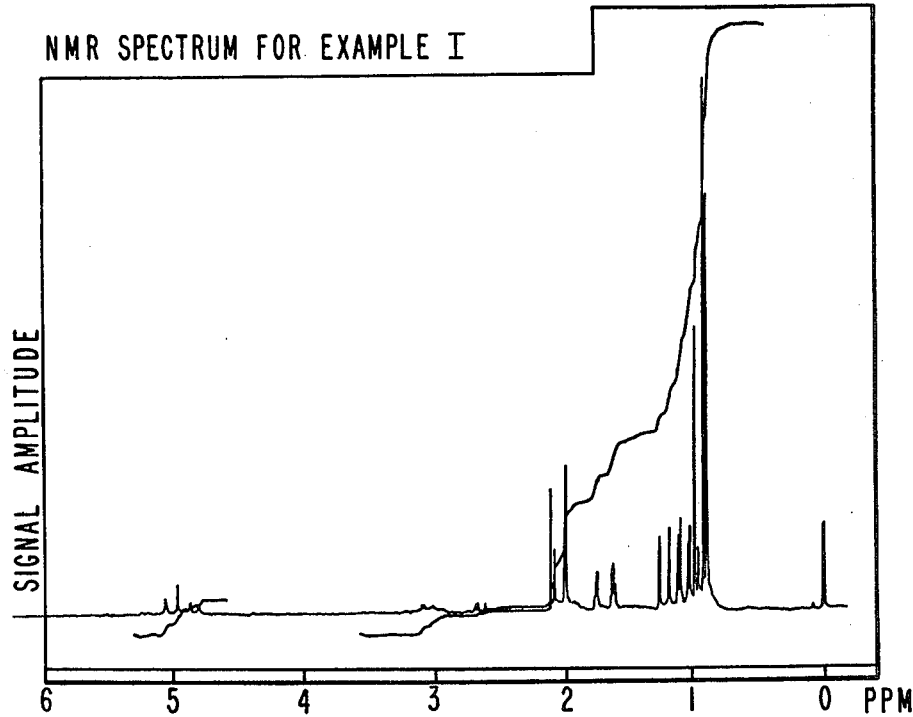

FIG. 2J represents the NMR spectrum for a mixture of compounds having the structures:

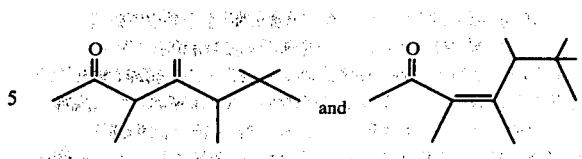

produced according to Example I.

Figure 2K:
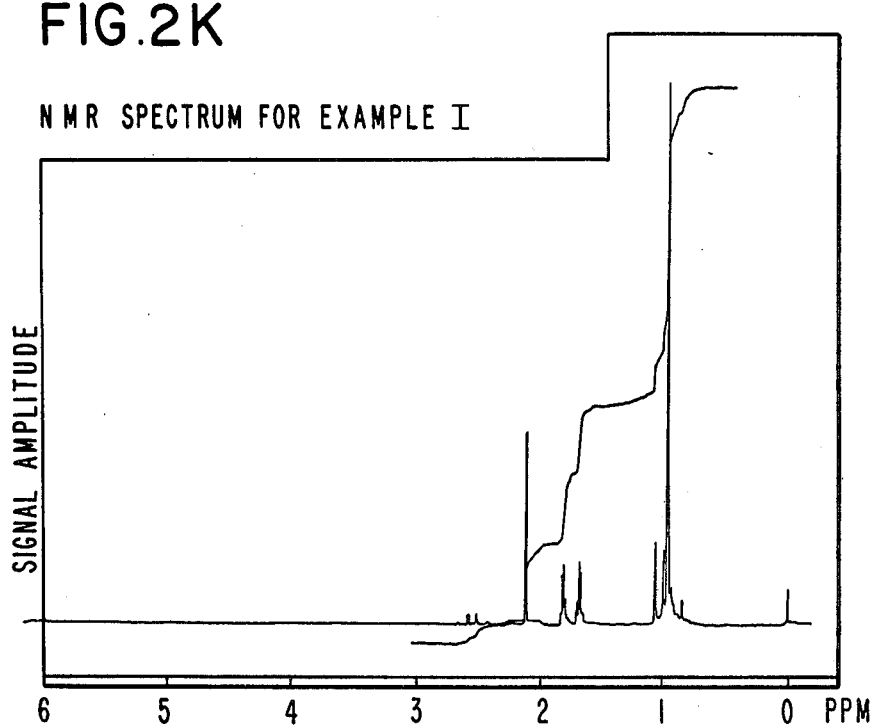

FIG. 2K represents the NMR spectrum for the compound having the structure:

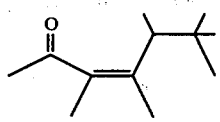

produced according to Example I.

Figure 2L:
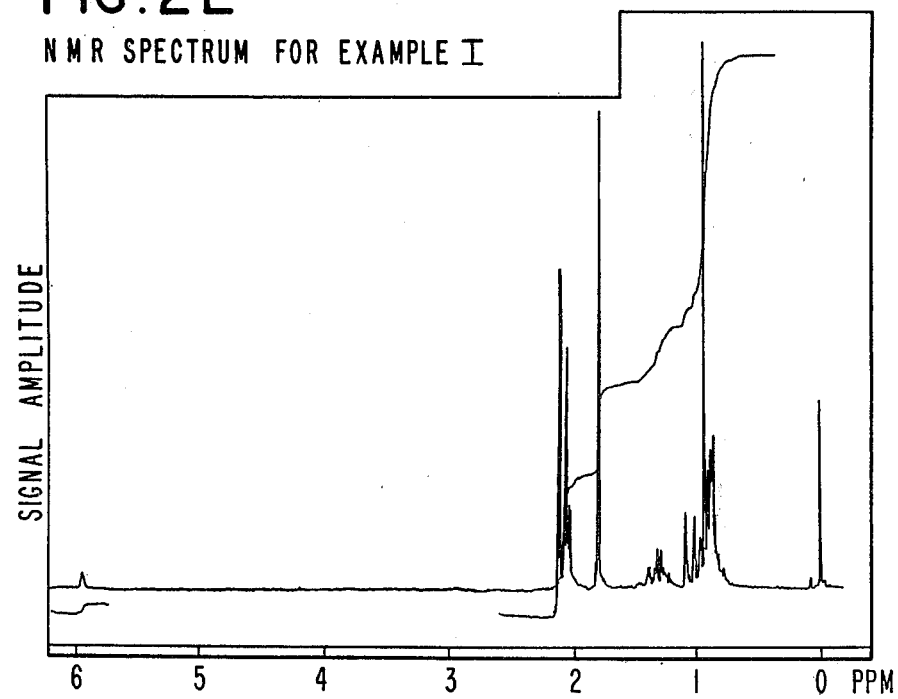

FIG. 2L represents the NMR spectrum for the compound containing the structure:

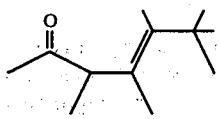

produced according to Example I.

Figure 3:
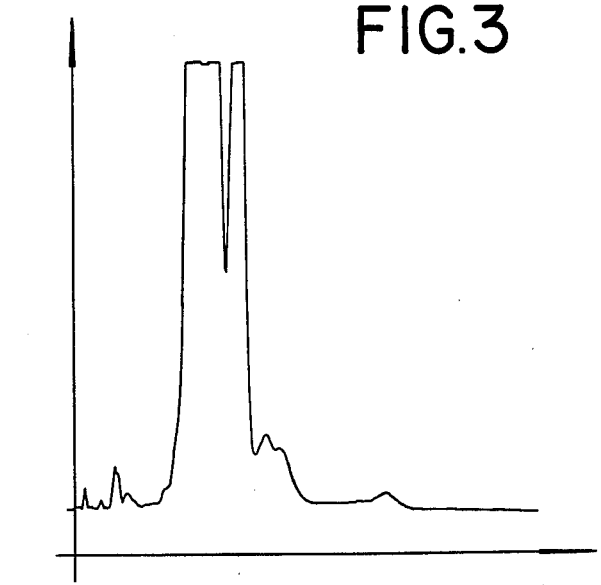

FIG. 3 represents the GLC profile for the reaction product of Example II(A) containing structures defined according to the genus having the structure:

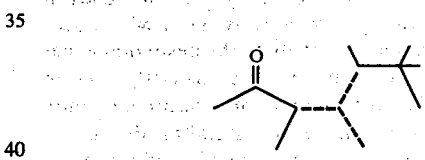

wherein in each of the molecules of the mixture, one of the dashed lines represents a carbon-carbon double bond and each of the other of the dashed lines represent carbon-carbon single bonds.

Figure 4:
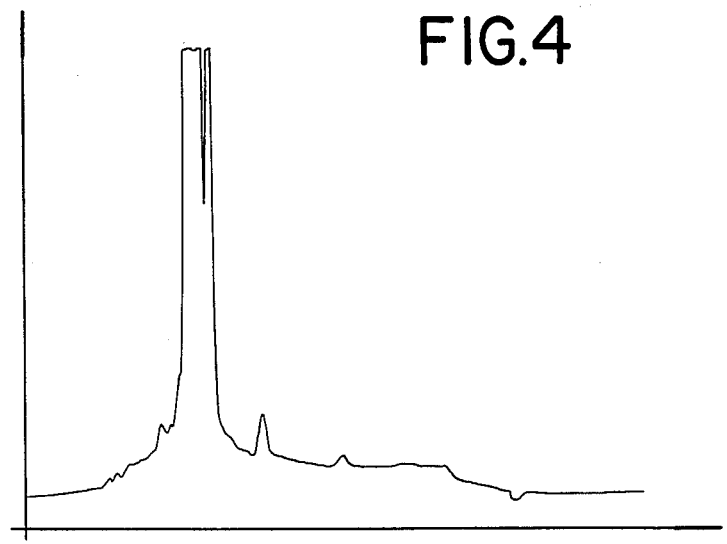

FIG. 4 represents the GLC profile for the reaction product of Example II(B) containing a mixture of compounds defined according to the structure:

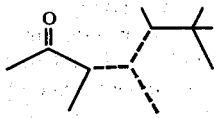

wherein in each of the molecules of the mixture, one of the dashed lines represents a carbon-carbon double bond and each of the other of the dashed lines represent carbon-carbon single bonds.

Figure 5:
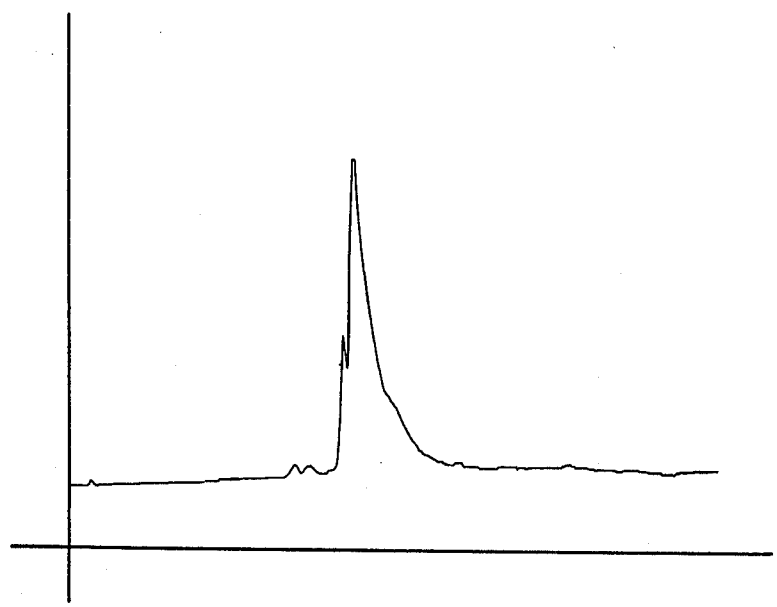

FIG. 5 is the GLC profile for the reaction product mixture prepared according to Example III (conditions: SF 96 column, 6'×¼"; programmed at 100°–220° C. at 8° C. per minute).

Figure 6:
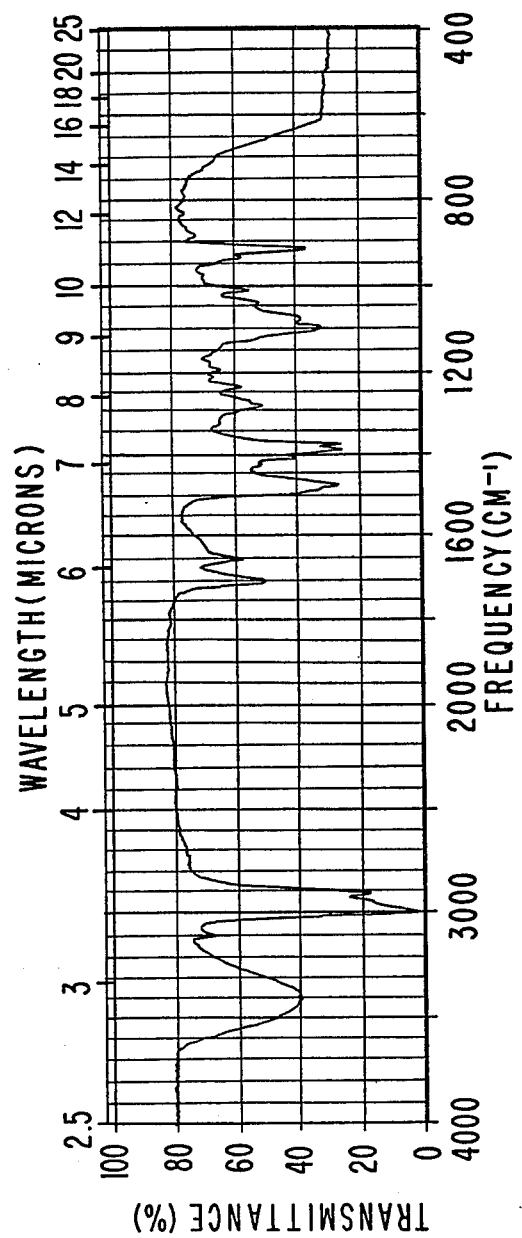

FIG. 6 is the infra-red spectrum for the reaction product mixture prepared according to Example III containing compounds defined according to the structure:

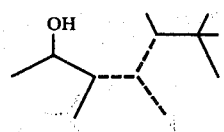

wherein in each of the molecules of the mixture, one of the dashed lines represents a carbon-carbon double bond and each of the other of the dashed lines represents carbon-carbon single bonds.

FIG. 7 is the GLC profile for the reaction product of Example IV(A), the formate ester mixture, containing compounds defined according to the structure:

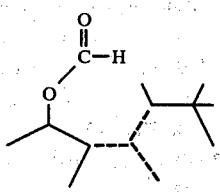

wherein in each of the molecules of the mixture, one of the dashed lines represents a carbon-carbon double bond and each of the other of the dashed lines represent carbon-carbon single bonds (conditions: 12% SF 96 column, 6'×¼", programmed at 100°–220° C. at 8° C. per minute).

FIG. 8 is the GLC profile for the distillation product (fraction 5) of the reaction product of Example IV(B) containing a mixture of compounds defined according to the structure:

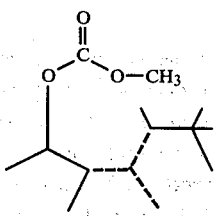

wherein in the mixture, in each of the molecules one of the dashed lines represents a carbon-carbon double bond and each of the other of the dashed lines represent carbon-carbon single bonds (conditions: 12% SF 96 column, 6'×¼" programmed at 100°–220° C. at 8° C. per minute).

Figure 9:
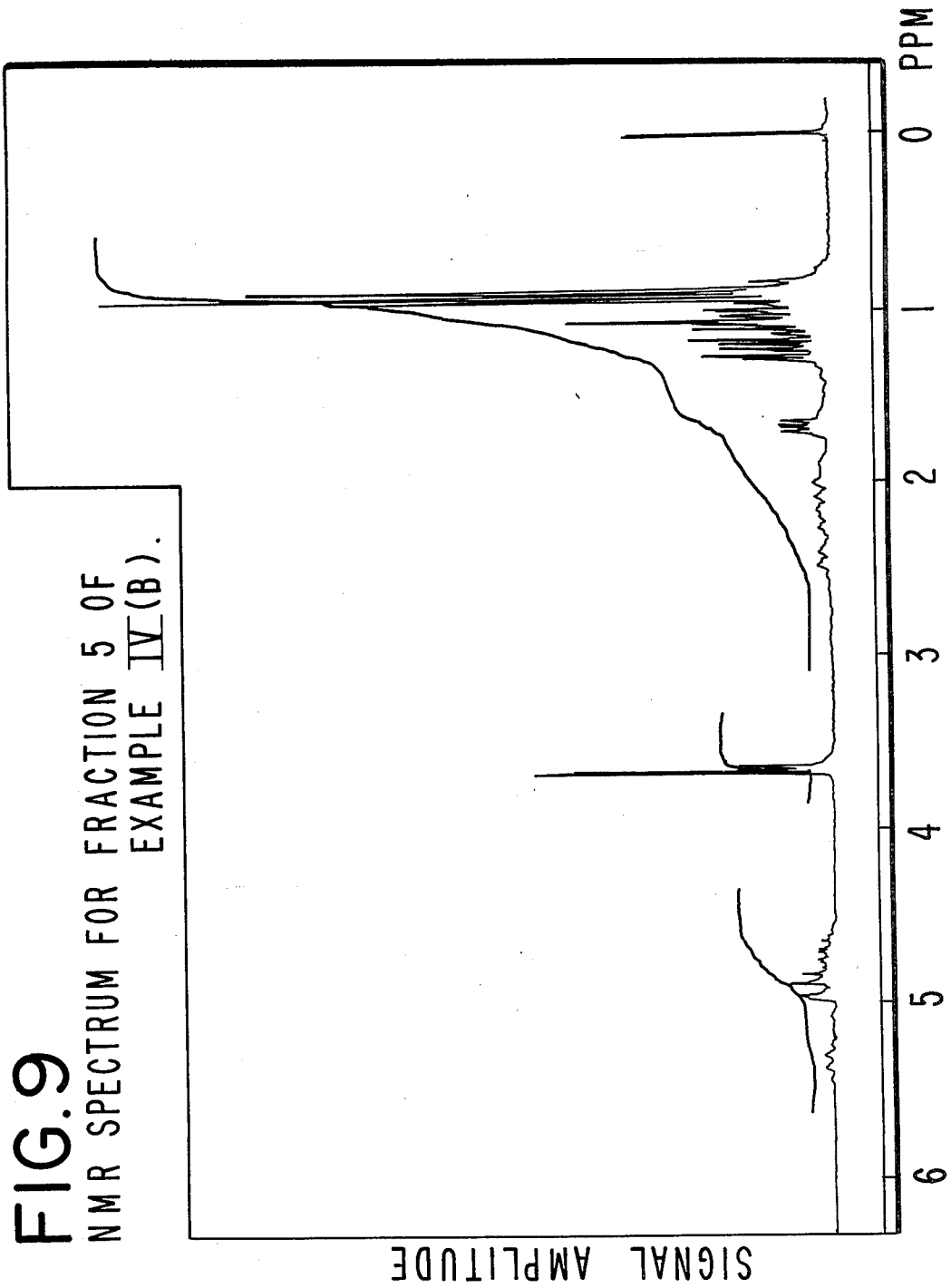

FIG. 9 is the NMR spectrum for fraction 5 of the distillation product of the reaction product of Example IV(B) containing a mixture of compounds defined according to the structure:

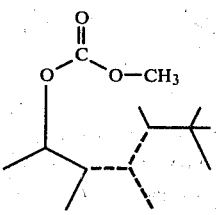

wherein in the mixture, in each of the molecules one of the dashed lines represents a carbon-carbon double bond and each of the other of the dashed lines represent carbon-carbon single bonds.

Figure 10:
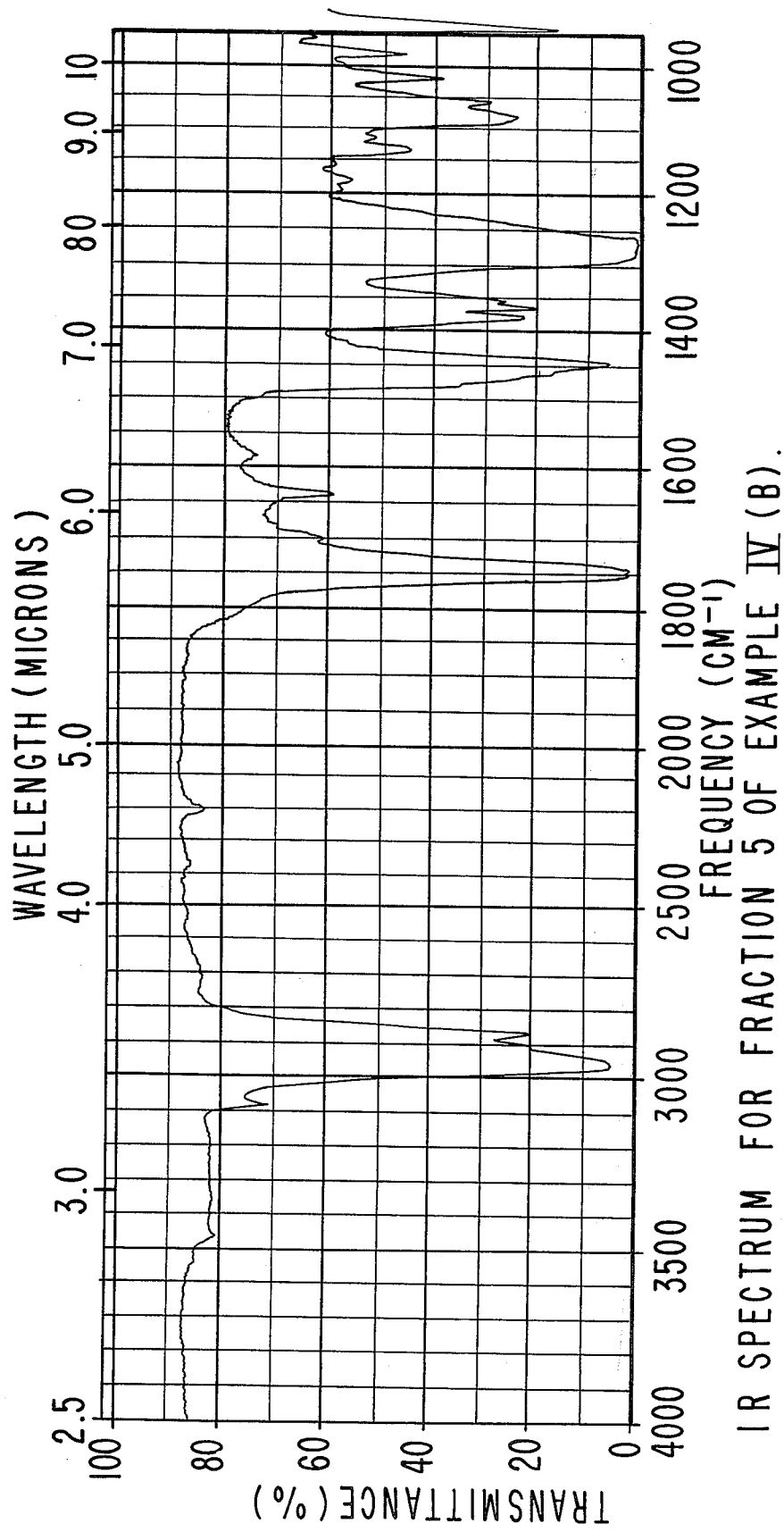

FIG. 10 is the infra-red spectrum for fraction 5 of the distillation product of the reaction product of Example IV(B) containing a mixture of compounds defined according to the structure:

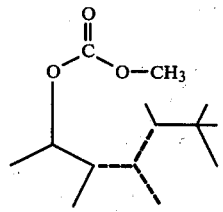

wherein in the mixture, in each of the molecules one of the dashed lines represents a carbon-carbon double bond and each of the other of the dashed lines represent carbon-carbon single bonds.

DETAILED DESCRIPTION OF THE DRAWINGS

FIG. AE represents the GLC profile for the reaction product of Example A wherein a sulfuric acid catalyst catalyzes the dimerization of isoamylene to form diisoamylene in the presence of an alpha-methyl styrene diluent according to the conditions of United Kingdom Patent Specification No. 796,130. Peak 301 has been determined by analysis to be the compound having the structure:

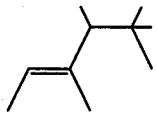

Peak 302 of the GLC profile contains the compounds having the structures:

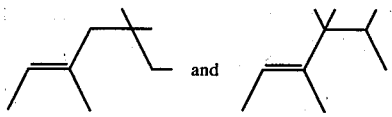

DISCLOSURES INCORPORATED BY REFERENCE HEREIN

The following applications for United States Letters Patent are incorporated by reference herein:

(a) U.S. Application for Letters Patent Ser. No. 160,788 filed on June 19, 1980 now U.S. Pat. No. 4,287,084 issued on Sept. 1, 1981 (entitled: "USE OF MIXTURE OF ALIPHATIC $C_{10}$ BRANCHED OLEFINS IN AUGMENTING OR ENHANCING THE AROMA OF PERFUMES AND/OR PERFUMED ARTICLES") setting forth the use of the compounds having the structures:

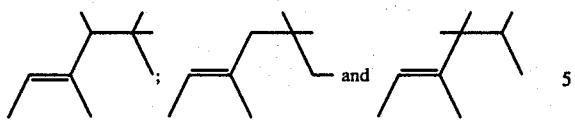

or generically, the compounds defined according to the structure:

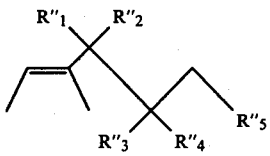

wherein $R_1''$, $R_2''$, $R_3''$, $R_4''$ and $R_5''$ represent hydrogen or methyl with three of $R_1''$, $R_2''$, $R_3''$, $R_4''$ and $R_5''$ representing methyl and the other two of $R_1''$, $R_2''$, $R_3''$, $R_4''$ and $R_5''$ representing hydrogen;

(b) Application for U.S. Letters Patent Ser. No. 188,576 filed on Sept. 18, 1980, now U.S. Pat. No. 4,303,555 issued on Dec. 1, 1981 a continuation-in-part of Ser. No. 160,788 filed on June 19, 1980; now U.S. Pat. No. 4,287,084 issued on Sept. 1, 1981 and Application for U.S. Letters Patent Ser. No. 184,132 filed on Sept. 4, 1980, now U.S. Pat. No. 4,321,255 issued on Mar. 23, 1982 entitled "BRANCHED KETONES; ORGANOLEPTIC USES THEREOF AND PROCESS FOR PREPARING SAME" disclosing the reaction:

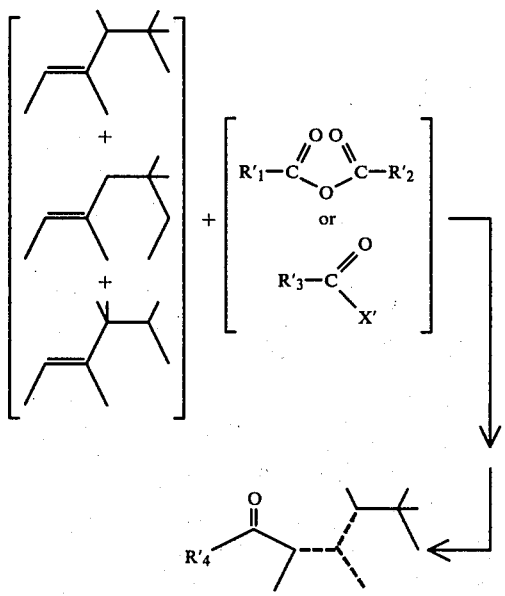

wherein $R_1'$, $R_2'$ and $R_3'$ represent $C_1$–$C_3$ lower alkyl and $R_4'$ is either of $R_1'$, $R_2'$ and $R_3'$ and wherein $X'$ is chloro or bromo, and the use of the resulting compounds for their organoleptic properties.

(d) Application for U.S. Letters Patent Ser. No. 252,334 filed on Apr. 9, 1981 now U.S. Pat. No. 4,336,164 issued on June 22, 1982 is directed to the use of the compounds defined according to the generic structure:

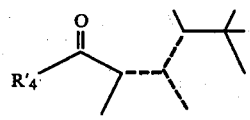

as starting materials wherein $R_4'$ is $C_1$–$C_3$ lower alkyl and wherein one of the dashed lines represents a carbon-carbon double bond and each of the other of the dashed lines represent carbon-carbon single bonds produced according to the process of Application for United States Letters Patent Ser. No. 184,132 filed on Sept. 4, 1980 now U.S. Pat. No. 4,321,255 issued on Mar. 23, 1982 entitled: "BRANCHED KETONES, ORGANOLEPTIC USES THEREOF AND PROCESS FOR PREPARING SAME".

(e) Application for U.S. Letters Patent Ser. No. 252,334 filed on Apr. 9, 1981, now U.S. Pat. No. 4,336,164 issued on June 22, 1982 discloses the use of certain branched chain olefinic secondary alcohols having the generic structure:

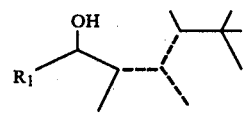

wherein $R_1$ represents methyl or isopropyl, which compounds are capable of imparting a variety of flavors and fragrances to various consumable materials. In this compound, one of the dashed lines represents a carbon-carbon double bond and each of the other of the dashed lines represent carbon-carbon single bonds.

THE INVENTION

The present invention provides compounds defined according to the structure:

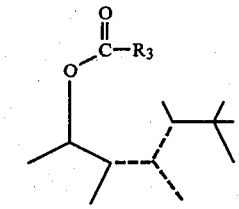

wherein $R_3$ represents hydrogen or methoxy and wherein one of the dashed lines represents a carbon-carbon double bond and each of the other of the dashed lines represent carbon-carbon single bonds. The present invention also provides an economical, efficient process for synthesizing the compound having the structure:

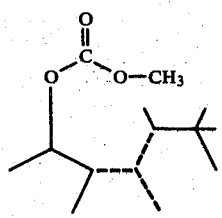

by reacting dimethyl carbonate with the formate ester of diisoamylene methyl carbinol in the presence of an alkali metal alkoxide according to the reaction:

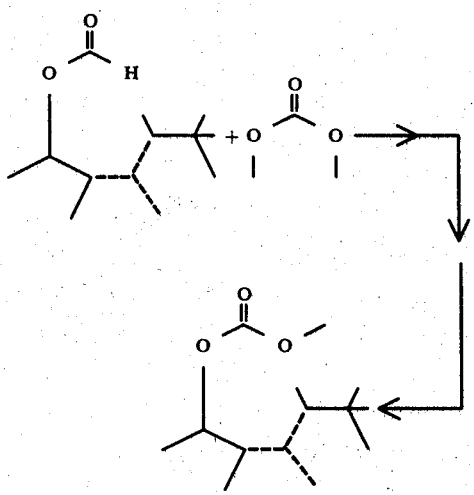

The present invention also provides processes for using the compounds defined according to the generic structure:

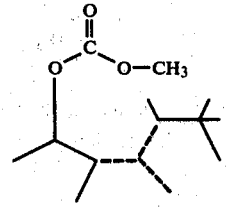

wherein one of the dashed lines represents a carbon-carbon double bond and each of the other of the dashed lines represent carbon-carbon single bonds for their organoleptic properties in augmenting or enhancing the organoleptic properties of consumable materials, that is, the aroma of perfumes, colognes, and perfumed articles (such as perfumed polymers, solid or liquid cationic, anionic, nonionic or zwitterionic detergents, soaps, fabric softener compositions, fabric softener articles including drier-added fabric softener articles such as BOUNCE ® (registered trademark of the Procter & Gamble Company of Cincinnati, Ohio), fabric brighteners, cosmetic powders, bath preparations, hair preparations such as hair sprays and shampoos).

The branched chain alkenyl carbonates of our invention are either usable in admixture with one another, or the isomers are usable in admixture with one another such as mixtures of compounds defined according to the structure:

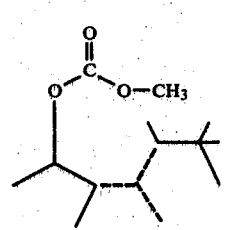

wherein one of the dashed lines in each of the molecules of the mixture represents a carbon-carbon double bond and each of the other of the dashed lines in each of the molecules of the mixture represent carbon-carbon single bonds, or they may be used as individual compounds which are, for example, defined according to the structures such as:

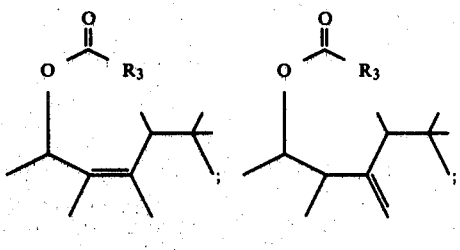

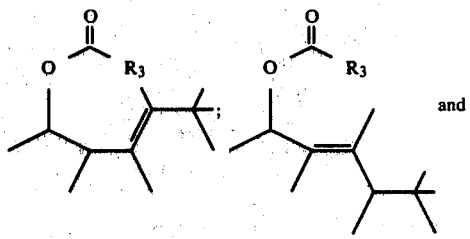

and

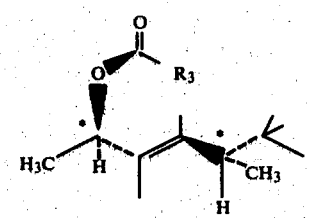

wherein $R_3$ is methoxy and wherein the compound having the structure:

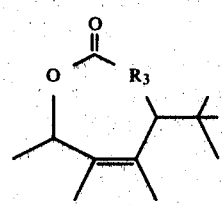

differs from the compound having the structure:

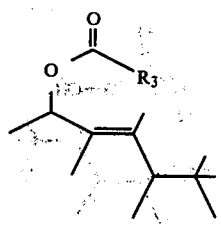

one of the structures being "cis" with respect to the methyl groups on the carbon atoms which make up the carbon-carbon double bond and the other of the structures being "trans" with respect to the methyl groups on the carbon atoms which make up the carbon-carbon double bond and wherein the structure:

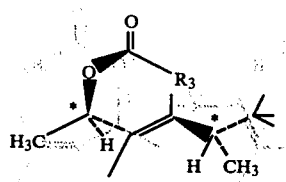

represents a "trans" isomer with respect to the methyl moieties bonded to the carbon atoms making up the carbon-carbon double bond and wherein the structure:

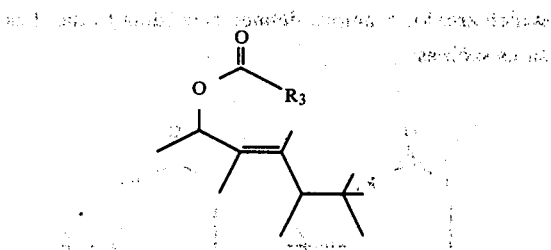

represents a stereo isomeric configuration wherein the carbon atoms having the "*" are assymetric carbon atom in the molecule and wherein the compound is a "trans isomer" with respect to the methyl moieties bonded to the carbon atoms which make up the carbon-carbon double bond.

The branched chain olefinic carbonates of our invention are obtained by means by first reacting ketones produced according to applications for United States Letters Patent Ser. No. 148,132 filed on Sept. 4, 1980 entitled: "BRANCHED KETONES, ORGANOLEPTIC USES THEREOF AND PROCESS FOR PREPARING SAME" with a reducing agent such as:

(a) one or more alkali metal borohydrides, e.g. sodium borohydride, lithium borohydride and potassium borohydride;
(b) hydrogen, using a catalyst such as 5% palladium on carbon, 5% palladium on calcium carbonate or palladium on barium sulfate (e.g. "Lindlar Catalyst"); or
(c) lithium aluminum hydride;
(d) aluminum alkoxides, such as aluminum isopropyxide and aluminum secondary epoxide, according to the reaction:

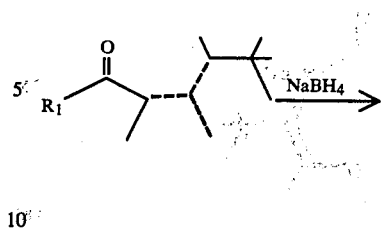

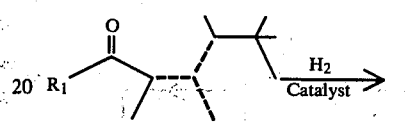

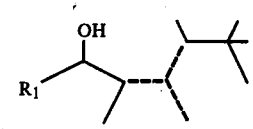

or, in general,

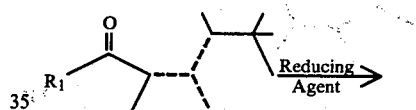

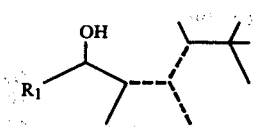

wherein $R_1$ represents methyl and then reacting the resulting alcohol with formic acid to form the formate according to the reaction:

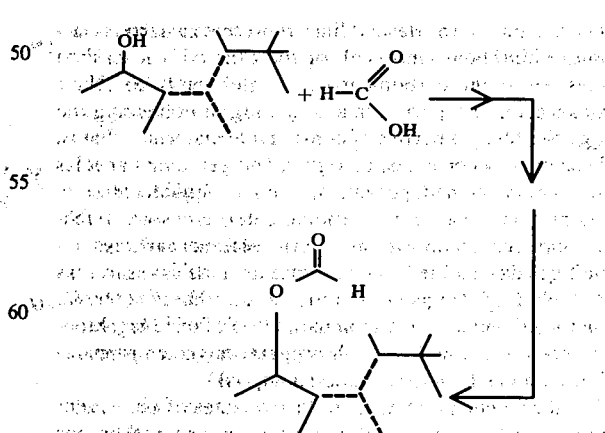

and finally reacting the resulting formate with dimethyl carbonate according to the reaction:

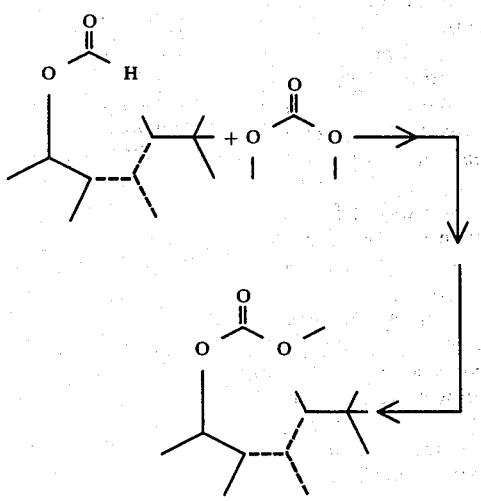

wherein in each of the molecules, one of the dashed lines represents a carbon-carbon double bond and each of the other of the dashed lines represent carbon-carbon single bonds.

When carrying out the reaction for reacting the ketone having the structure:

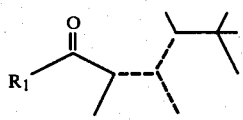

with an alkali metal borohydride such as sodium borohydride, the reaction is carried out in the presence of a protic solvent which reacts relatively slowly or not at all with the alkali metal borohydride when compared to the reaction of the alkali metal borohydride with the ketone having the structure:

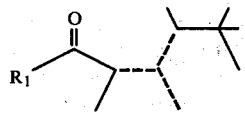

Specific workable solvents which must "solvate" the carbonyl moiety in order to enable the reaction to proceed at a reasonable rate are isopropyl alcohol, n-propenol, n-butanol, isobutyl alcohol and p-butyl alcohol.

The temperature of reaction is necessarily a function of:
(i) the yield desired;
(ii) the time of reaction;
(iii) the nature of the solvent used;
(iv) the pressure of the vapor over the reaction mass;
(v) the concentration of the reactant, the alkali metal borohydride and the ketone having the structure:

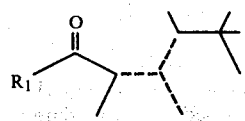

in the solvent;
(vi) the desired rate of reaction, and
(vii) the ratio of alkali metal borohydride:ketone having the structure:

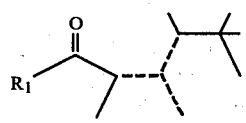

It is preferred to carry out the reaction at reflux conditions at atmospheric pressure. Thus, when using isopropyl alcohol as a solvent where the mole ratio of alkali metal borohydride:ketone having the structure:

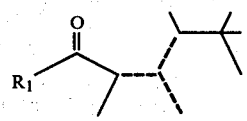

is 1:2, the temperature of reaction is about 73° C. and the time of reaction is 3 hours. In the case of using an alkali metal borohydride, the alcohol acts as a "solvent" and not as a "reactant".

On the other hand, when using the aluminum alkoxide such as aluminum secondary butoxide and aluminum isopropoxide, the solvent must be a source of hydrogen which is the actual reducing agent in the reaction. Thus, it is necessary that the "solvent" be a "reactable solvent" such as isopropyl alcohol and not merely a solvating solvent.

The mole ratio of alkali metal borohydride:ketone having the structure:

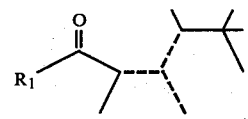

is preferably 1:2, which means that the equivalent ratio regarding hydrogen:ketone is 2:1; that is, the alkali metal borohydride is in 100% excess since theoretically only one mole of the alkali metal borohydride is needed to react with 4 moles of ketone, since one mole of alkali metal borohydride provides 4 atoms of hydrogen. interestingly and surprisingly in this reaction and in all of the above reactions, the double bond does get reduced during the reaction.

Insofar as the hydrogenation reaction is concerned with the ketone having the structure:

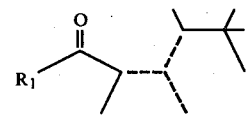

as the starting material or one of the ketones defined according to the structure:

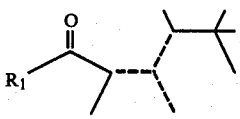

as being a starting material, the ketone is reacted with hydrogen in the presence of a Raney Nickel catalyst or a palladium on carbon catalyst or a "Lindlar" catalyst (palladium on calcium carbonate) or palladium on barium sulfate. The percentage of palladium in the palladium on carbon catalyst or in the palladium on calcium carbonate catalyst or in the palladium on barium sulfate catalyst varies from about 2% up to about 7% with a percentage of palladium in the palladium on carbon catalyst or in the palladium on calcium carbonate catalyst or in the palladium on barium sulfate catalyst being preferred to be 5%. The temperature of reaction for the hydrogenation may vary from about 10° C. up to about 100° C. with a preferred reaction temperature of 25° C.-35° C. Since the reaction is exothermic, it is usually necessary to provide external cooling to the reaction mass during the course of the reaction. The pressure of hydrogen over the reaction mass may vary from about 5 psig up to about 100 psig with the most preferred pressure being 20 psig. Pressures greater than 150 psig will give rise to amounts of fully saturated alcohol. The hydrogenation reaction may be carried out in the presence of or in the absence of a solvent. When a solvent is used, it is required that it be an inert (non-reactive) solvent such as isopropyl alcohol, hexane or ethanol. If a solvent is used, it is preferred that the mole ratio of solvent:ketone having the structure:

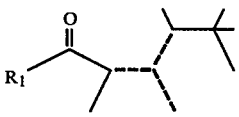

be approximately 1:1. When a palladium containing catalyst is used, the percentage of catalyst in the reaction mass may vary from 0.125% up to about 2.0% with a percentage of catalyst of about 0.25% being preferred. Where a Raney Nickel catalyst is used, the percentage of catalyst in the reaction mass may vary from about 3% up to about 10% with a percentage of catalyst of about 5% being preferred.

If the reaction is carried out in the presence of the alkali metal borohydride, the reaction mass is neutralized using weak acid and the reaction product is then further washed with water and, if necessary, sodium carbonate. In any event, the reaction mass is ultimately distilled fractionally to yield the desired saturated alcohol product having the generic structure:

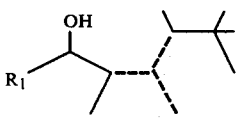

wherein $R_1$ is methyl or isopropyl and one of the dashed lines represents a carbon-carbon double bond and the other of the dashed lines represent carbon-carbon single bonds.

The reaction to form the formate ester is carried out by reacting formic acid with the resulting alcohol in the presence of a protonic acid catalyst such as 98% sulfuric acid or phosphoric acid. The reaction preferably takes place at reflux conditions in the presence of an inert solvent such as toluene or xylene. When using toluene as a solvent and operating at atmospheric pressure, the temperature of reaction, at reflux, is 92°-98° C. The mole ratio of formic acid:alcohol is preferably in the range of from 1 up to 1.5:1 with a mole ratio of formic acid:alcohol of 1:0.85 being preferred (based on 100% formic acid). Commercial formic acid is 90% formic acid. At the end of the reaction, the reaction mass is washed with water and the excess acid is neutralized. The solvent is stripped off and the reaction product is preferably used "as is" in the reaction of the formate with the dimethyl carbonate.

The reaction of the resulting formate with dimethyl carbonate according to the reaction:

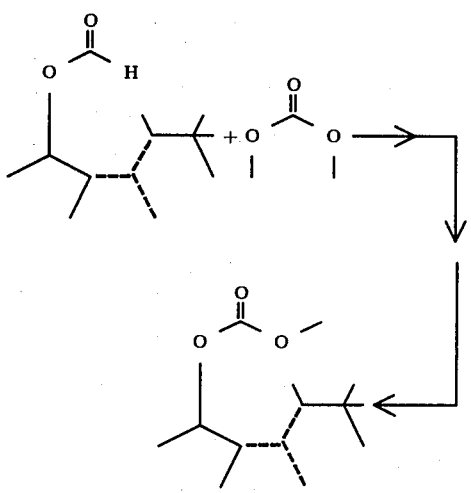

takes place in the presence of an alkali metal alkoxide such as sodium methoxide, sodium ethoxide, sodium t-butoxide, potassium methoxide, potassium ethoxide and potassium t-butoxide. This reaction between the formate ester and the dimethyl carbonate takes place in the absence of any additional solvent. The mole ratio range of dimethyl carbonate:formate ester may vary from 3 moles dimethyl carbonate:0.5 moles formate ester down to 1 mole dimethyl carbonate:1 mole formate ester. It is preferred that the mole ratio of dimethyl carbonate:formate ester be about 2:1. The concentration in the reaction mass of alkali metal alkoxide catalyst may vary from about 0.005 up to about 0.01 with a mole ratio of about 0.05 being preferred.

The reaction temperature range may vary from about 50° C. up to about 100° C. and the reaction pressure may vary from atmospheric pressure up to 10 atmospheres. Higher temperature of reaction necessitates higher pressure over the reaction mass in order to prevent the reaction product from evaporating therefrom.

At the end of the reaction, the reaction product is purified according to standard procedures such as fractional distillation and, if necessary, chromatographic separation as by high pressure liquid chromatography or GLC (vapor phase chromatography).

The branched chain olefinic methyl carbonates of our invention can be used to contribute myrrh-like, labdanum-like aroma nuances to perfume compositions, perfumed articles such as solid or liquid cationic, nonionic, anionic or zwitterionic detergents, perfumed polymers, fabric softener compositions, fabric softener articles, optical brighteners, fabric conditioners, hair preparations, shampoos and hair sprays. As olfactory agents, the branched chain olefinic methyl carbonates of our invention can be formulated into or used as components of a "perfume composition".

The term "perfume composition" is used herein to mean a mixture of organic compounds including, for example, alcohols, aldehydes, ketones, nitriles, ethers, lactones, esters other than the carbonates of our invention, and frequently hydrocarbons which are admixed so that the combined odors of the individual components produce a pleasant or desired fragrance. Such perfume compositions usually contain: (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation and (d) top notes which are usually low-boiling, fresh-smelling materials.

In perfume compositions, the individual component will contribute its particular olfactory characteristics, but the overall effect of the perfume composition will be the sum of each of the effects of each of the ingredients. Thus, the individual compounds of this invention or mixtures thereof can be used to alter the aroma characteristics of the perfume composition, for example, by highlighting or moderating the olfactory reaction contributed by another ingredient in the composition.

The amount of branched chain olefinic methyl carbonate of our invention which will be effective in perfume compositions depends upon many factors including the other ingredients, their amounts and the effects which are desired. It has been found that perfume compositions containing as little as 0.1% of the branched chain olefinic methyl carbonates of our invention or even less and perfume compositions containing as much as 70% of the branched chain olefinic methyl carbonates of our invention can be used to impart interesting myrrh-like, labdanum-like aroma nuances to perfumed articles, perfume compositions and colognes. Such perfumed articles include fabric softener compositions, drier-added fabric softener articles, cosmetic powders, talc, solid or liquid anionic, cationic, nonionic or zwitterionic detergents and perfumed polymers. The amount employed can range up to 70% and will depend on considerations of cost, nature of the end product and the effect desired on the finished product and particular fragrance sought.

Thus, the branched chain olefinic methyl carbonates of our invention can be used alone or in a perfume composition as an olfactory component, in solid or liquid anionic, cationic, nonionic or zwitterionic detergents (including soaps), perfumed polymers (those which are microporous and those which are macroporous and contain particulate absorbent fillers such as talc or calcium carbonate), space odorants and deodorants; perfumes, colognes, toilet waters, bath salts, hair preparations such as lacquers, brilliantines, pomades and shampoos; cosmetic preparations such as creams, deodorants, hand lotions and sun screens; powders such as talcs, dusting powders, face powders and the like.

When used as an olfactory component of a perfumed article such as a microporous polymer or a macroporous polymer containing an absorbent filler or such as a solid or liquid cationic, anionic, nonionic or zwitterionic detergent or of a cosmetic powder, as little as 0.01% of the branched chain olefinic methyl carbonates of our invention will suffice to provide an interesting myrrh-like, labdanum-like aroma. Generally no more than 0.8% of the branched chain olefinic methyl carbonates of our invention are required in the perfumed article.

In addition, the perfume compositions of our invention can contain a vehicle or carrier for the branched chain olefinic methyl carbonates of our invention, alone, or with other ingredients. The vehicle can be a liquid such as an alcohol such as ethanol, a glycol such as propylene glycol or the like. The carrier can be an absorbent solid such as a gum (e.g. xanthan gum, gum arabic or guar gum) or components for encapsulating the composition as by coacervation (using gelatin) or as by shell polymerization around the liquid fragrance center using a urea formaldehyde prepolymer.

The following Examples A, I, II, III and IV set forth processes required to prepare the branched chain olefinic methyl carbonates of our invention. The examples following Example IV, Examples V et seq. represent methods for using the branched chain olefinic methyl carbonates of our invention for their organoleptic properties.

Unless otherwise indicated, all parts and percentages are by weight.

EXAMPLE A

Preparation of Diisoamylene

Reaction:

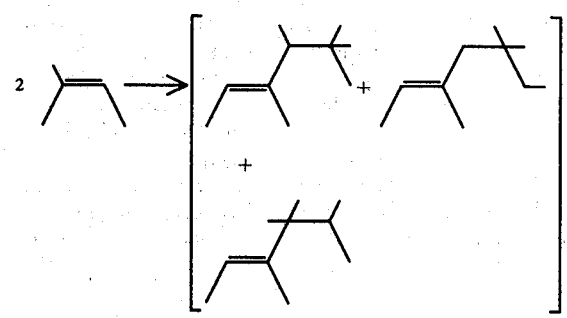

Diisoamylene is prepared according to one of the procedures set forth in the following references:
(i) Murphy & Lane, Ind. Eng. Chem., Prod. Res. Dev., Vol. 14, No. 3, 1975 p. 167 (Title: Oligomerization of 2-Methyl-2-Butene in Sulfuric Acid and Sulfuric-Phosphoric Acid Mixtures).
(ii) Whitmore & Mosher, Vol. 68, J. Am. Chem. Soc., February, 1946, p . 281 (Title: The Depolymerization of 3,4,5,5-Tetramethyl-2-hexene and 3,5,5-Trimethyl-2-heptene in Relation to the Dimerization of Isoamylenes).
(iii) Whitmore & Stahly, Vol. 67, J. Am. Chem. Soc., December, 1945; p. 2158 (Title: The Polymerization of Olefins. VIII The Polymerization of Olefins in Relation to Intramolecular Rearrangements. II).
(iv) U.S. Pat. No. 3,627,700 issued on Dec. 14, 1971, (Zuech).
(v) U.S. Pat. No. 3,538,181 issued on Nov. 3, 1970, (Banks).
(vi) U.S. Pat. No. 3,461,184 issued on Aug. 12, 1969 (Hay, et al), (vii) Gurwitsch, Chemische Berichte, 1912, Vol. 2, p. 796 (Production of Di-isoamylene From Isoamylene Using Mercury Acetate Catalyst).

As an illustration, and not by way of limitation, the following example sets forth the preparation of diisoamylenes useful in producing the fragrance materials of our invention.

Over a period of ten hours, 2-methyl-2-butene is pumped through a 5'×⅝ (0.625 inch) tube packed with 15.0 grams of polystyrene sulfonic acid catalyst at a temperature of 100° C. and at a pressure of 400 psig.

The resulting material was distilled in a fractionation column in order to separate the diisoamylene from the higher molecular weight polymers, which are formed during the reaction as by-products. This material distills at 36°–40° C. vapor temperature; 74°–94° C. liquid temperature and 4–5 mm/Hg pressure.

FIG. AA represents the GLC profile for the reaction product of this Example A using a 70% sulfuric acid catalyst at 35° C.

FIG. AB represents the GLC profile for the reaction product of this Example A using an Amberlyst® 15 acidic ion exchange resin catalyst at a temperature of 150° C.

FIG. AC represents the GLC profile for the reaction product of this Example A, using an Amberlyst® 15 catalyst at 100° C.

FIG. AD represents the GLC profile for the reaction product of this Example A, using a sulfuric acid catalyst and an alpha-methylstyrene diluent at 35° C. according to the conditions of United Kingdom Patent Specification 796,130 (crude reaction product).

FIG. AE represents the GLC profile for the reaction product of this Example A, using a sulfuric acid catalyst at 35° C. and an alpha-methylstyrene diluent according to the conditions of United Kingdom Patent Specification No. 796,130 (distilled reaction product). Distillation range: 36°–40° C. vapor temperature; 74°–94° C. liquid temperature and 4–5 mm/Hg pressure.

FIG. BA represents the NMR spectrum for peak 301 of the GLC profile of FIG. AE. Peak 301 has been determined by analysis to be the compound having the structure:

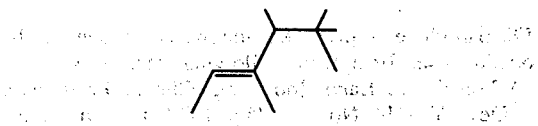

FIG. BB represents the infra-red spectrum for peak 301 of the GLC profile of FIG. AE.

FIG. CA represents the NMR spectrum for peak 302 of the GLC profile of FIG. AE. Peak 302 contains the compounds having the structures:

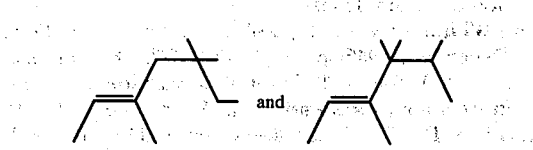

FIG. CB represents the infra-red spectrum for peak 302 of the GLC profile of FIG. AE.

FIG. D represents the NMR spectrum for peak 302 of the GLC profile of FIG. AB.

EXAMPLE I

Preparation of Acetyl Derivative of Diisoamylene

Reaction:

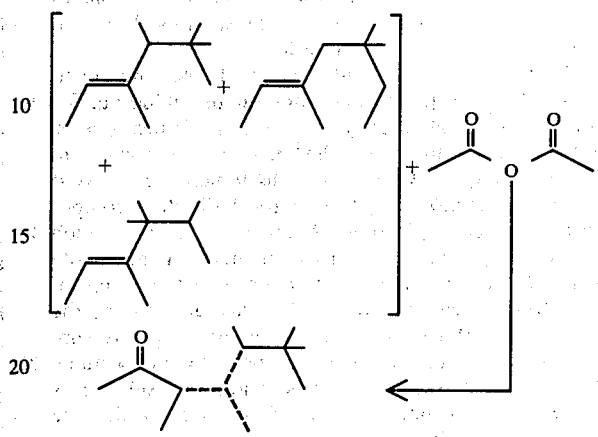

wherein in each of the structures containing dashed lines, these structures represent mixtures of molecules wherein in each of the molecules, one of the dashed lines respresents a carbon-carbon double bond and each of the other of the dashed lines respresent carbon-carbon single bonds.

Into a 2-liter reaction flask equipped with stirrer, thermometer, reflex condenser and heating mantle, is placed 1000 g of acetic anhydride and 80 g of boron trifluoride diethyl etherate. The resulting mixture is heated to 80° C. and, over a period of 40 minutes, 690 g of diisoamylene prepared according to the illustration in Example A, supra, (distilling at 36°–40° C. vapor temperature; 74°–94° C. liquid temperature and 4–5 mm/Hg pressure) is added.

The reaction mass is maintained at 82°–85° C. for a period of 5.5 hours, whereupon it is cooled to room temperature. The reaction mass is then added to one liter of water and the resulting mixture is stirred thereby yielding two phases; an organic phase and an aqueous phase. The organic phase is separated from the aqueous phase and neutralized with two liters of 12.5% sodium hydroxide followed by one liter of saturated sodium chloride solution. The resulting organic phase is then dried over anhydrous sodium sulfate and distilled in a one plate distillation column, yielding the following fractions:

| Fraction No. | Vapor Temp. (°C.) | Liquid Temp. (°C.) | mm/Hg Pressure | Weight of Fraction (g.) |
|---|---|---|---|---|
| 1 | 33/68 | 62/77 | 8/8 | 161 |
| 2 | 69 | 79 | 4 | 100 |
| 3 | 72 | 86 | 3.0 | 191 |
| 4 | 88 | 134 | 3.0 | 189 |

The resulting material is then distilled on a multi-plate fractionation column, yielding the following fractions at the following reflux ratios:

| Fraction No. | Vapor Temp. (°C.) | Liquid Temp. (°C.) | mm/Hg Pressure | Reflux Ratio R/D | Weight of Fraction (g.) |
|---|---|---|---|---|---|
| 1 | 30/65 | 62/83 | 5/5 | 9:1 | 30.8 |

-continued

| Fraction No. | Vapor Temp. (°C.) | Liquid Temp. (°C.) | mm/Hg Pressure | Reflux Ratio R/D | Weight of Fraction (g.) |
|---|---|---|---|---|---|
| 2 | 68 | 84 | 5 | 9:1 | 52.8 |
| 3 | 68 | 85 | 5 | 9:1 | 34 |
| 4 | 69 | 87 | 5 | 9:1 | 43 |
| 5 | 69 | 87 | 5 | 9:1 | 34 |
| 6 | 71 | 88 | 4 | 4:1 | 41 |

| Fraction No. | Vapor Temp. (°C.) | Liquid Temp. (°C.) | mm/Hg Pressure | Reflux Ratio R/D | Weight of Fraction (g.) |
|---|---|---|---|---|---|
| 7 | 70 | 88 | 5 | 4:1 | 36.5 |
| 8 | 71 | 91 | 5 | 4:1 | 42 |
| 9 | 73 | 95 | 3 | 4:1 | 42.5 |
| 10 | 80 | 106 | 3 | 4:1 | 39 |
| 11 | 80 | 142 | 3 | 4:1 | 50.8 |
| 12 | 80 | 220 | 3 | 4:1 | 24 |

GLC, NMR, IR and mass spectral analyses yield the information that the resulting material is a mixture of cis and trans isomers having a generic structure:

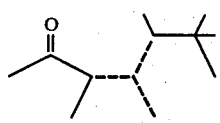

wherein in each of the molecules, one of the dashed lines is a carbon-carbon double bond and the other of the dashed lines is a carbon-carbon single bond and, primarily, this mixture contains the molecular species (cis and trans isomers) as follows:

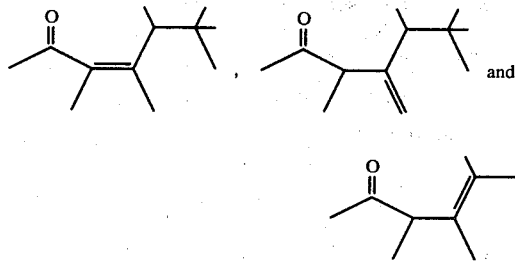

Fractions 2-12 are bulked for use in the following reaction in Examples II(A) and II(B).

FIG. 1 sets forth the GLC profile for the reaction product of Example I, containing compounds defined according to the structure:

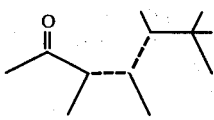

wherein in each molecule of the mixture, one of the dashed lines is a carbon-carbon double bond and the other of the dashed lines are carbon-carbon single bonds.

FIG. 2A represents the infra-red spectrum of Peak 3 of the GLC profile of FIG. 1.

FIG. 2B represents the infra-red spectrum of Peak 4 of the GLC profile of FIG. 1.

FIG. 2C represents the infra-red spectrum for Peak 5 of the GLC profile of FIG. 1.

FIG. 2D represents the infra-red spectrum for Peak 7 of the GLC profile of FIG. 1.

FIG. 2E represents the infra-red spectrum for Peak 7 of the GLC profile of FIG. 1.

FIG. 2F represents the infra-red spectrum for Peak 8 of the GLC profile of FIG. 1.

FIG. 2G represents the infra-red spectrum for Peak 9 of the GLC profile of FIG. 1.

FIG. 2H represents the infra-red spectrum for Peak 10 of the GLC profile of FIG. 1.

FIG. 2J represents the NMR spectrum for a mixture of compounds having the structures:

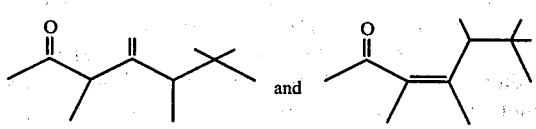

produced according to Example I.

FIG. 2K represents the NMR spectrum for the compound having the structure:

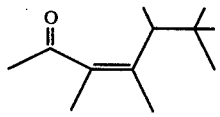

produced according to Example I.

FIG. 2L represents the NMR spectrum for the compound containing the structure:

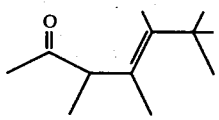

produced according to Example I.

EXAMPLE II

Preparation of Acetyl Derivative of Diisoamylene

Reaction:

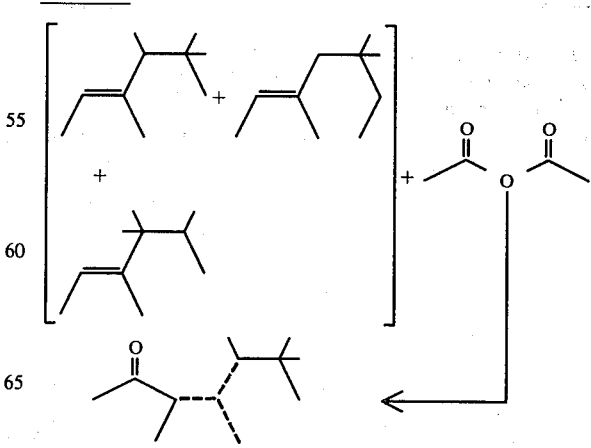

EXAMPLE II(A)

Into a 5-liter reaction flask equipped with electric stirrer, thermometer, addition funnel, 24/42 y-tube, condenser, heating mantle and nitrogen purge accessories are added 41 ml of 70% methane sulfonic acid followed by 30 grams of phosphorous pentoxide. The resulting mixture exotherms to 60° C.

Over a period of 7 minutes, 235 ml of acetic anhydride is added to the reaction mass while maintaining same at a temperature of 65° C. Over a period of 30 minutes while maintaining the reaction temperature at 80° C., 516 ml of diisoamylene prepared according to the illustration of Example A is added dropwise to the reaction mass. At the end of the addition of the diisoamylene, GLC analysis indicates 42% product.

The reaction mass is added to a 5 gallon open head separatory flask containing 1 liter of water.

The resulting mixture is washed with 1 liter of 12% sodium hydroxide followed by 1 liter of saturated sodium chloride solution. 100 ml toluene is added to help separation.

GLC, NMR, IR and mass spectral analyses yield the information that the resulting organic phase is a mixture of compounds defined according to the generic structure:

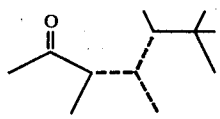

wherein in each of the molecules one of the dashed lines is a carbon-carbon double bond and the other two of the dashed lines represent carbon-carbon single bonds.

The resulting reaction product is then dried over anhydrous magnesium sulfate and distilled on a 3-inch stone column yielding the following fractions:

| Fraction No. | Vapor Temp. (°C.) | Liquid Temp. (°C.) | mm/Hg Pressure |
|---|---|---|---|
| 1 | 65/65 | 103/92 | 113/35 |
| 2 | 60 | 80 | 1 |
| 3 | 52 | 89 | 1 |
| 4 | 61 | 134 | 1 |
| 5 | 73 | 140 | 1 |

Fractions 2, 3 and 4 are bulked and are used in the syntheses in subsequent examples.

FIG. 3 represents the GLC profile for the reaction product of Example II(A) containing the structures defined according to the genus having the structure:

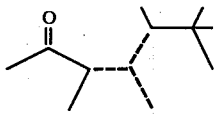

wherein in each of the molecules of the mixture, one of the dashed lines represents a carbon-carbon double bond and each of the other of the dashed lines represent carbon-carbon single bonds.

EXAMPLE II(B)

To a 500 ml reaction flask equipped with reflux condenser, addition funnel, thermometer, Thermowatch, heating mantle, cooling bath and nitrogne purge accessories, is added 406 ml of acetic anhydride and 30 ml boron trifluoride etherate. The reaction mass is heated to 60° C. and while maintaining the reaction mass at 60° over a period of 30 minutes, diisoamylene, prepared according to the illustration of Example A is added. The resulting reaction mass is then heated, with stirring at 60° C. for a period of 12 hours. At the end of the 12 hour period, the reaction mass is distilled yielding the following fractions:

| Fraction No. | Vapor Temp. (°C.) | Liquid Temp. (°C.) | mm/Hg pressure | Weight of Fraction (g.) |
|---|---|---|---|---|
| 1 | 50/58 | 60/70 | 2.5 | 330 |
| 2 | 67 | 87 | 1.4 | 329 |
| 3 | 71 | 88 | 3.0 | 65 |
| 4 | 90 | 115 | 3.0 | 195 |

Fractions 2, 3 and 4 are bulked for use in subsequent examples.

The resulting mass, by GLC, IR, NMR and mass spectral analyses consist of compounds defined according to the generic structure:

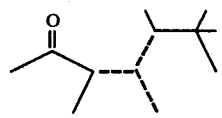

wherein in each of the molecules one of the dashed lines is a carbon-carbon double bond and the other two of the dashed lines represent carbon-carbon single bonds.

FIG. 4 sets forth the GLC profile for the reaction product of this Example II(B).

EXAMPLE III

Preparation of Diisoamylene Methyl Carbinol

Reaction:

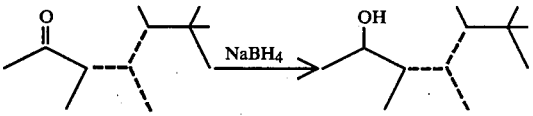

Into a 2 liter reaction flask equipped with reflux condenser, addition funnel, thermometer, heating mantle, and nitrogen bleed is placed 1 liter of isopropyl alcohol followed by 38 grams of sodium borohydride. The resulting mixture is heated to reflux and over a period of 40 minutes while maintaining the reflux temperature at 48° C. dropwise addition of acetyl diisoamylene according to Example I (368 grams) (bulked fractions 2-12 of the distillation) is carried out.

At the end of the addition of the 368 grams of acetyl diisoamylene, the reaction mass is stirred at a temperature of 73° C. for a period of 3 hours. The reaction mass is then transferred to a separatory flask containing 1 liter of water. 200 ml 5% hydrochloric acid is added to the separatory funnel and the organic layer is separated from the inorganic layer.

The organic layer is washed with one liter of sodium carbonate and is then distilled on a 1" packed stone column yielding the following fractions:

| Fraction Number | Vapor Temp. (°C.) | Liquid Temp. (°C.) | Pressure mm/Hg |
|---|---|---|---|
| 1 | 25/20 | 18/20 | 10 |
| 2 | 80 | 90 | .2 |
| 3 | 81 | 92 | .2 |
| 4 | 83 | 96 | .2 |
| 5 | 81 | 130 | .2 |
| 6 | 80 | 200 | .2 |

Fractions 2–4 are bulked for use in the synthesis in subsequent examples.

The resulting product (bulked fractions 2–4) is analyzed by GLC, NMR and IR analysis to contain a mixture of compounds defined according to the structure:

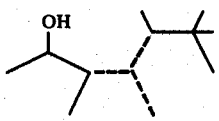

wherein in each of the compounds one of the dashed lines represents a carbon-carbon double bond and each of the other of the dashed lines represent carbon-carbon single bonds.

FIG. 5 is the GLC profile of the reaction product (conditions: 6'×¼" SF 96 column programmed at 100°–120° C. at 8° C. per minute).

FIG. 6 is the infra red spectrum for the distillation product, bulked fractions 2–4.

EXAMPLE IV

Preparation of the Methyl Carbonate of Diisoamylene Methyl Carbinol

Reactions:

EXAMPLE IV(A)

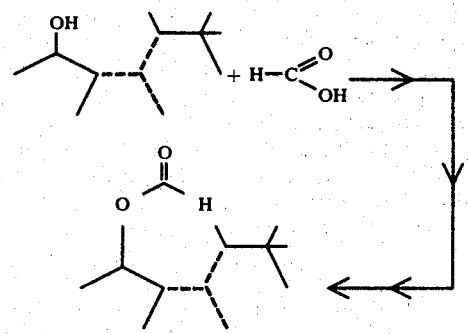

EXAMPLE IV(B)

-continued

Reactions:

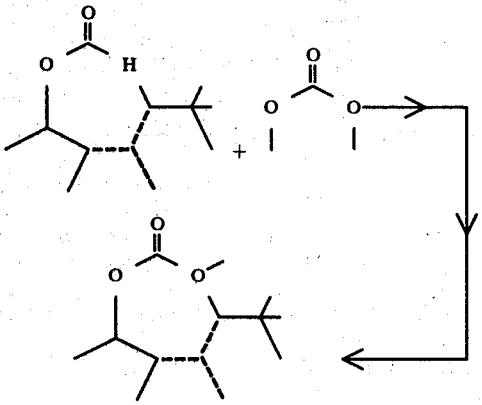

EXAMPLE IV(A)

Into a 1 liter reaction flask equipped with nitrogen blanket apparatus and Bidwell trap, and reflux condenser, stirrer and thermometer is placed 159 grams of diisoamylene methyl carbinol produced according to Example III (bulked fractions 2–4) (0.85 moles); 55.2 grams of 90% formic acid (1.1 moles); 1 ml of 98% sulfuric acid and 250 ml toluene.

The reaction mass is heated to reflux (92°–97° C.) and maintained at a temperature in the range of 92°–97° C. for a period of 2 hours. At the end of the 2 hour period, the reaction mass is washed with the following materials:

(i) 500 ml water;
(ii) 500 ml water;
(iii) 500 ml saturated sodium chloride;
(iv) 500 ml saturated sodium chloride.

The solvent is stripped from the reaction mass on a rotary evaporator and GLC, NMR, IR and mass spectral analyses indicate that the yield is 54%.

The resulting product is then used in the procedure of Example IV(B).

EXAMPLE IV(B)

Into a 1 liter reaction flask equipped with thermometer, reflux condenser, heating mantle, Bidwell trap and nitrogen blanket apparatus is placed a mixture of 5 grams of sodium methoxide and 97 grams (1.04 moles) of dimethyl carbonate. 20 ml of the formate ester prepared in Example IV(A), supra, is then added to the mixture and the mixture is heated to 80° C. While maintaining the reaction mass at 78°–80° C., the remaining formate ester (total: 208 grams; 0.52 moles) is added. The reaction mass is then heated at a temperature in the range of 88°–104° C. over a period of 4 hours.

At the end of the reaction, the reaction mass is transferred to a separatory funnel and is washed with 2 one-liter portions of water followed by 0.5 liters of saturated sodium chloride. The reaction mass is then distilled on a 6" stone packed column yielding the following fractions:

| Fraction Number | Vapor Temp. (°C.) | Liquid Temp. (°C.) | Pressure mm/Hg. | Weight of Fraction (grams) |
|---|---|---|---|---|
| 1 | 43/58 | 79/89 | 4/2.1 | 40 |
| 2 | 75 | 97 | 3.2 | 22 |
| 3 | 87 | 101 | 3.2 | 25 |

-continued

| Fraction Number | Vapor Temp. (°C.) | Liquid Temp. (°C.) | Pressure mm/Hg. | Weight of Fraction (grams) |
|---|---|---|---|---|
| 4 | 88 | 103 | 3.2 | 18 |
| 5 | 90 | 113 | 3.2 | 22 |
| 6 | 83 | 160 | 3.2 | 29 |

FIG. 8 is the GLC profile for fraction 5 of the foregoing distillation (conditions: 12% SF-96 6'×¼" column programmed at 100°-220° C. at 8° C. per minute).

FIG. 9 is the NMR spectrum for fraction 5 of the foregoing distillation.

FIG. 10 is the infra-red spectrum for fraction 5 of the foregoing distillation.

Fraction 5 has an excellent myrrh, labdanum aroma profile.

EXAMPLE V

Chypre Perfume Base

The following chypre perfume formulation is prepared:

| Ingredients | Parts by Weight |
|---|---|
| Sandalwood oil (Haiti) | 220 |
| Bergamot oil | 227 |
| Rose absolute | 50 |
| Oil of coriander | 25 |
| Methyl jasmonate | 50 |
| Patchouli oil | 40 |
| Red thyme oil | 7 |
| Vetiver oil Bourbon | 110 |
| Diisoamylene methyl carbinol methyl carbonate prepared according to Example IV(B), fraction 5 of distillation | 55 |
| Oakmoss absolute | 110 |
| Castorium resinoid | 70 |
| Neroli oil | 20 |
| Isosafrole | 1 |
| Musk ambrette | 15 |
| Civetone | 5 |

The use of the carbonate produced according to Example IV(B) imparts an excellent labdanum topnote with myrrh-like undertone to this chypre base formulation.

EXAMPLE VI

Opoponax Perfume Formulation

The following perfume formulation is prepared:

| Ingredients | Parts by Weight |
|---|---|
| Bergamot oil | 300 |
| Orris oil | 50 |
| Opoponax resinoid | 50 |
| Lemon oil | 20 |
| Jasmin natural | 50 |
| Bulgarian rose oil | 80 |
| Ginger oil | 10 |
| Diisoamylene methyl carbinol methyl carbonate prepared according to Example IV(B) | 150 |
| Galbanum resin | 40 |
| Vetiver oil | 25 |
| Violet essence | 50 |
| Costus oil | 50 |
| 2,3,8,8-tetramethyl-2-acetyl-delta 9,10-octahydro naphthalene | 200 |

The use of the carbonate prepared according to Example IV(B), fraction 5, imparts to this apoponax perfume formulation an excellent myrrh undertone with labdanum-like topnotes.

The carbonate ester of Example IV(B) can be used to replace the myrrh resinoid necessary for this opoponax formulation. Indeed, an improvement occurs when the carbonate ester is used in place of the myrrh resinoid formulation as a result of the labdanum-like nuances imparted.

EXAMPLE VII

Preparation of Cosmetic Powder Compositions

Cosmetic powder compositions are prepared by mixing in a ball mill 100 grams of talcum powder with 0.25 grams of each of the substances set forth in Table I below. Each of the cosmetic powder compositions has an excellent aroma as described in Table I below.

TABLE I

| Substance | Aroma Description |
|---|---|
| Diisoamylene methyl carbinol methyl carbonate prepared according to Example IV(B), fraction 5 | A myrrh, labdanum aroma with high intensity and long lasting power. |
| Fragrance formulation of Example V | A chypre like essence with labdanum topnotes and myrrh-like undertones. |
| Fragrance formulation of Example VI | An opoponax aroma with myrrh undertones and pleasant labdanum-like topnotes. |

EXAMPLE VIII

Perfumed Liquid Detergents

Concentrated liquid detergents (lysine salt of n-dodecylbenzene sulfonic acid as more specifically described in U.S. Pat. No. 3,948,818, issued on Apr. 6, 1976 incorporated by reference herein) with aroma nuances as set forth in Table I of Example VII, are prepared containing 0.10%, 0.15%, 0.20%, 0.25%, 0.30% and 0.35% of the substance set forth in Table I of Example VII. They are prepared by adding and homogeneously mixing the appropriate quantity of substance set forth in Table I of Example VII in the liquid detergent. The detergents all possess excellent aromas as set forth in Table I of Example VII, the intensity increasing with greater concentrations of substance as set forth in Table I of Example VII.

EXAMPLE IX

Preparation of Colognes and Handkerchief Perfumes

Compositions as set forth in Table I of Example VII are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table I of Example VII are imparted to the colognes and to the handkerchief perfumes at all levels indicated.

EXAMPLE X

Preparation of Soap Compositions

One hundred grams of soap chips [per sample] (IVORY ®, produced by the Procter & Gamble Company of Cincinnati, Ohio), are each mixed with one gram samples of substances as set forth in Table I of Example VII until homogeneous compositions are obtained. In each of the cases, the homogeneous compositions are heated under 8 atmospheres pressure at 180° C. for a period of three hours and the resulting liquids are placed into soap molds. The resulting soap cakes, on cooling, manifest aromas as set forth in Table I of Example VII.

EXAMPLE XI

Preparation of Solid Detergent Compositions

Detergents are prepared using the following ingredients according to Example I of Canadian Pat. No. 1,007,948 (incorporated by reference herein):

| Ingredient | Percent by Weight |
|---|---|
| "Neodol® 45-11" (a $C_{14}$-$C_{15}$ alcohol ethoxylanted with 11 moles of ethylene oxide) | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table I of Example VII. Each of the detergent samples has an excellent aroma as indicated in Table I of Example VII.

EXAMPLE XII

Utilizing the procedure of Example I at column 15 of U.S. Pat. No. 3,632,396 (the disclosure of which is incorporated herein by reference), nonwoven cloth substrates useful as drier-added fabric softening articles of manufacture are prepared wherein the substrate, the substrate coating, the outer coating and the perfuming material are as follows:
1. A water "dissolvable" paper ("Dissolvo Paper")
2. Adogen 448 (m.p. about 140° F.) as the substrate coating; and
3. An outer coating having the following formulation (m.p. about 150° F.):
    57% $C_{20-22}$ HAPS
    22% isopropyl alcohol
    20% antistatic agent
    1% of one of the substances as set forth in Table I of Example VII Fabric softening compositions prepared according to Example I at column 15 of U.S. Pat. No. 3,632,396 having aroma characteristics as set forth in Table I of Example VII, supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table I of Example VII is admixed in each case with the outer coating mixture, thereby providing a total aromatized outer coating weight ratio to substrate of about 0.5:1 by weight of the substrate. The aroma characteristics are imparted in a pleasant manner to the head space in a drier on operation thereof in each case using said drier-added fabric softener non-woven fabrics and these aroma characteristics are described in Table I of Example VII, supra.

EXAMPLE XIII

Hair Spray Formulations

The following hair spray formulation is prepared by first dissolving PVP/VA E-735 copolymer manufactured by the GAF Corporation of 140 West 51st Street, New York, N.Y., in 91.62 grams of 95% food grade ethanol. 8.0 grams of the polymer is dissolved in the alcohol. The following ingredients are added to the PVP/VA alcoholic solution:

| | |
|---|---|
| Dioctyl sebacate | 0.05 weight percent |
| Benzyl alcohol | 0.10 weight percent |
| Dow Corning 473 fluid (prepared by the Dow Corning Corporation) | 0.10 weight percent |
| Tween 20 surfactant (prepared by ICI America Corporation) | 0.03 weight percent |
| One of the perfumery substances as set forth in Table I of Example VII | 0.10 weight percent |

The perfuming substances as set forth in Table I of Example VII add aroma characteristics as set forth in Table I of Example VII which are rather intense and aesthetically pleasing to the users of the soft-feel, good-hold pump hair sprays.

EXAMPLE XIV

Conditioning Shampoos

Monamid CMA (prepared by the Mona Industries Company) (3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation) (1.4 weight percent). The resulting melt is admixed with Stepanol WAT produced by the Stepan Chemical Company (35.0 weight percent). The resulting mixture is heated to 60° C. and mixed until a clear solution is obtained (at 60° C.). This material is "COMPOSITION A".

Gafquat ® 755 N polymer (manufactured by GAF Corporation of 140 West 51st Street, New York, N.Y.) (5.0 weight percent) is admixed with 0.1 weight percent sodium sulfite and 1.4 weight percent polyethylene glycol 6000 distearate produced by Armak Corporation. This material is "COMPOSITION B".

The resulting COMPOSITION A & COMPOSITION B are then mixed in a 50:50 wt ratio of A:B and cooled to 45° C. and 0.3 wt percent of perfuming substance as set forth in Table I of Example VII is added to the mixture. The resulting mixture is cooled to 40° C. and blending is carried out for an additional one hour in each case. At the end of this blending period, the resulting material has a pleasant fragrance as indicated in Table I of Example VII.

EXAMPLE XV

A fabric conditioner produced according to the method of U.S. Pat. No. 4,291,072 issued on Sept. 22, 1981 is produced whereby the sheet consisting of nonwoven rayon substrate as set forth at column 3, lines 25–34 passed through the bath of molten cationic fabric softener-isopropenyl mixture is passed through the bath at 10 atmospheres pressure, during which time a fragrance material as set forth in Table I of Example VII is added at the rate of 0.35%. The resulting sheet when used with a clothing batch gives rise to a pleasant aroma in the head space above the clothing batch as set forth in Table I of Example VII.

What is claimed is:

1. An ester defined according to the structure:

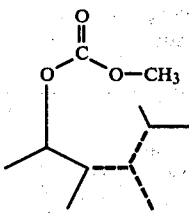

wherein one of the dashed lines represents a carbon-carbon double bond and each of the other of the dashed lines represent carbon-carbon single bonds.

2. A mixture produced according to the process of:
   (a) dimerizing isoamylene in order to form a mixture of diisoamylene isomers defined according to the structure:

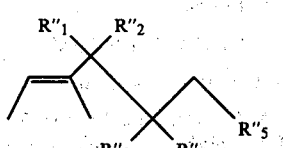

wherein $R_1''$, $R_2''$, $R_3''$, $R_4''$ and $R_5''$ represent hydrogen or methyl with three of $R_1''$, $R_2''$, $R_3''$, $R_4''$ and $R_5''$ representing methyl and the other two of $R_1''$, $R_2''$, $R_3''$, $R_4''$ and $R_5''$ representing hydrogen;
   (b) acetylating the resulting diisoamylene derivative with acetic anhydride or an acetyl halide in order to form a mixture of compounds defined according to the structure:

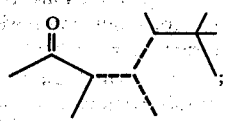

(c) reducing the resulting compound in order to form a mixture of carbinols defined according to the structure:

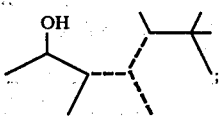

(d) reacting the resulting carbinol with formic acid in order to form a formate defined according to the structure:

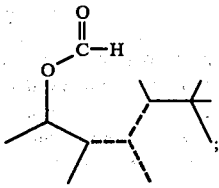

(e) reacting the resulting formate with dimethyl carbonate in order to form the compounds defined according to the structure:

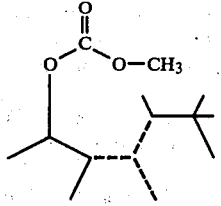

* * * * *